(12) United States Patent
Dixon

(10) Patent No.: US 9,575,304 B2
(45) Date of Patent: Feb. 21, 2017

(54) PATHOLOGY SLIDE SCANNERS FOR FLUORESCENCE AND BRIGHTFIELD IMAGING AND METHOD OF OPERATION

(71) Applicant: Arthur Edward Dixon, Waterloo (CA)

(72) Inventor: Arthur Edward Dixon, Waterloo (CA)

(73) Assignee: Huron Technologies International Inc., Waterloo, Ontario (CA)

( * ) Notice: Subject to any disclaimer, the term of this patent is extended or adjusted under 35 U.S.C. 154(b) by 0 days.

(21) Appl. No.: 13/730,488

(22) Filed: Dec. 28, 2012

(65) Prior Publication Data

US 2013/0342674 A1    Dec. 26, 2013

Related U.S. Application Data

(60) Provisional application No. 61/664,022, filed on Jun. 25, 2012.

(51) Int. Cl.
| | | |
|---|---|---|
| *G02B 21/36* | (2006.01) | |
| *G02B 21/00* | (2006.01) | |
| *G02B 21/12* | (2006.01) | |
| *G02B 5/20* | (2006.01) | |
| *G01N 21/64* | (2006.01) | |

(52) U.S. Cl.
CPC ............ *G02B 21/36* (2013.01); *G01N 21/6458* (2013.01); *G02B 5/201* (2013.01); *G02B 21/0076* (2013.01); *G02B 21/12* (2013.01); *G02B 21/367* (2013.01)

(58) Field of Classification Search
CPC ...................... H04N 2209/045; G01N 21/6456
See application file for complete search history.

(56) References Cited

U.S. PATENT DOCUMENTS

| | | | | |
|---|---|---|---|---|
| 6,339,217 | B1* | 1/2002 | Kley .............................. | 250/216 |
| 6,803,955 | B1* | 10/2004 | Yosida .......................... | 348/272 |
| 2004/0085462 | A1* | 5/2004 | Sasaki ......................... | 348/231.6 |
| 2006/0133657 | A1* | 6/2006 | Schmid ................ | G01N 15/042 382/128 |
| 2010/0329522 | A1* | 12/2010 | Otsuka .......................... | 382/128 |

* cited by examiner

*Primary Examiner* — Mikhail Itskovich
(74) *Attorney, Agent, or Firm* — Daryl W. Schnurr

(57) ABSTRACT

An instrument for scanning a specimen has a two-dimensional sensor array, the sensor array containing a mosaic color filter array or a scanning color filter array. The instrument can be operated in fluorescence or in brightfield. The scanning color filter array has the same color throughout each row with adjacent rows having different colors.

32 Claims, 19 Drawing Sheets

↑ Slide Motion

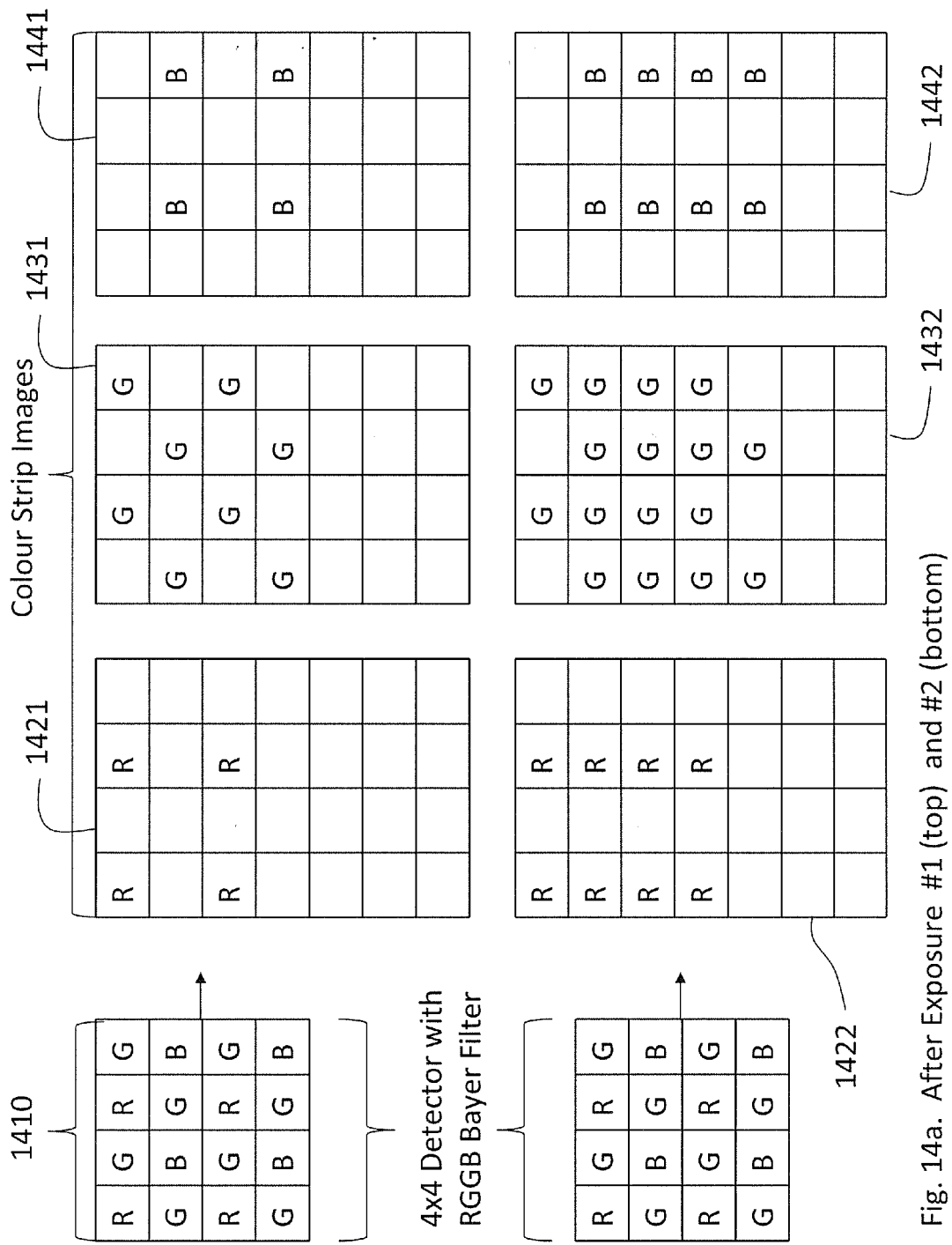
Fig. 14a. After Exposure #1 (top) and #2 (bottom)

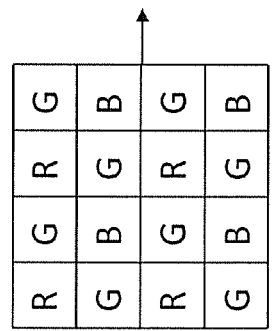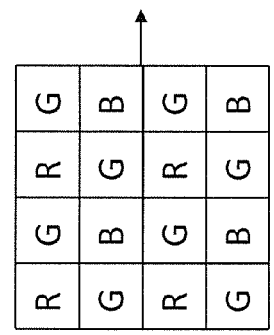
Fig. 14b. After Exposure #3 (top) and #4 (bottom)

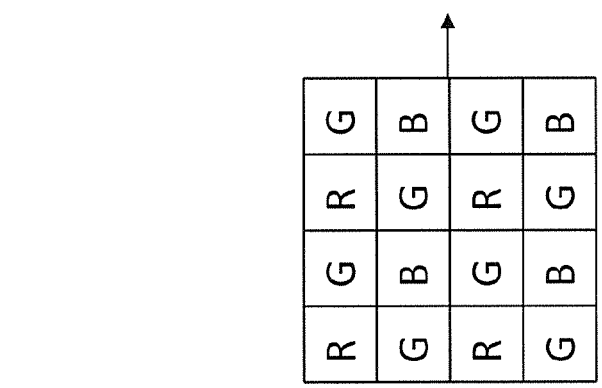
Fig. 14c. After Exposure #5

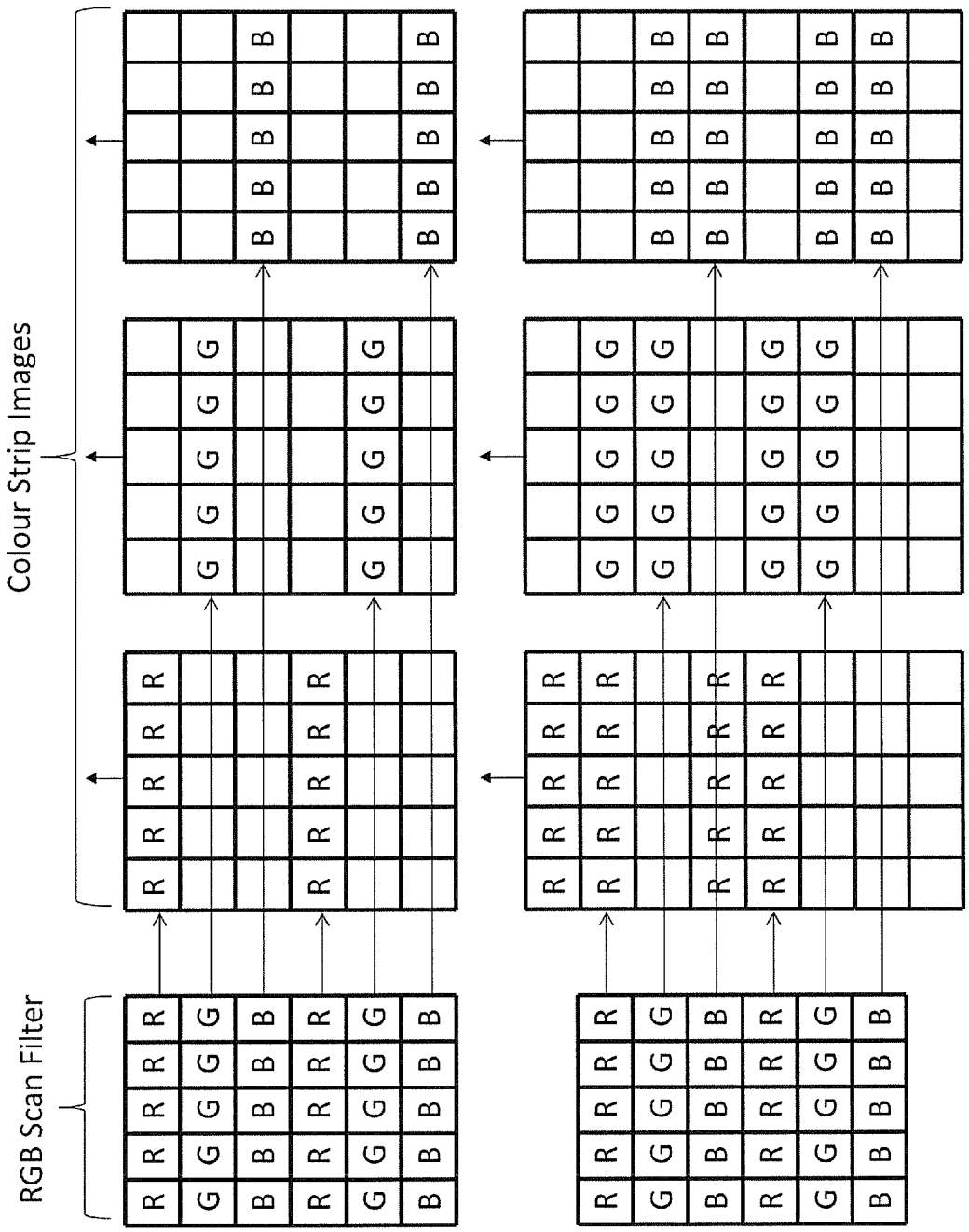
Fig. 15: First Exposure (top), Second Exposure (bottom)

Fig. 16: RGBW scan filter

Fig. 17: RWGWBW Scan Filter

PATHOLOGY SLIDE SCANNERS FOR FLUORESCENCE AND BRIGHTFIELD IMAGING AND METHOD OF OPERATION

BACKGROUND OF THE INVENTION

Field of the Invention

This invention relates to the fields of microscopic imaging of large specimens with particular emphasis on brightfield and fluorescence imaging, including photoluminescence and spectrally-resolved fluorescence. Applications include imaging tissue specimens, genetic microarrays, protein arrays, tissue arrays, cells and cell populations, biochips, arrays of biomolecules, detection of nanoparticles, photoluminescence imaging of semiconductor materials and devices, and many others.

Description of the Prior Art

The macroscope originally described in U.S. Pat. No. 5,381,224 is a scanning-laser system that uses a telecentric laser-scan lens to provide a wide field of view. Several embodiments are presently in use. These include instruments for fluorescence and photoluminescence (including spectrally-resolved) imaging (several other contrast mechanisms are also possible), instruments in which a raster scan is provided by the combination of a scanning mirror and a scanning specimen stage, instruments in which the specimen stage is stationary and the raster scan is provided by two scanning mirrors rotating about perpendicular axes, confocal and non-confocal versions, and other embodiments. A macroscope with fine focus adjustment was described in U.S. Pat. No. 7,218,446, and versions for reflected-light, fluorescence, photoluminescence, multi-photon fluorescence, transmitted-light, and brightfield imaging were described. The combination of a scanning laser macroscope with a scanning laser microscope to provide an imaging system with a wide field of view and the high resolution capability of a microscope was described in U.S. Pat. No. 5,532,873.

When the macroscope is used for fluorescence imaging, it has several advantages. Exposure for each fluorophore can be adjusted separately without changing scan speed by changing either laser intensity and/or detector gain (in the case of a detector comprised of a photomultiplier tube (pmt) followed by a preamplifier, both the pmt voltage (which changes pmt gain) and preamplifier gain can be changed). The ability to adjust the detection gain for each fluorophore separately allows the instrument to simultaneously collect multiple fluorophore images that are all correctly exposed. In addition, the appropriate laser wavelength can be provided to excite a chosen fluorophore, and excitation wavelengths can be chosen so they do not overlap detection wavelength ranges.

Several other technologies are used for imaging large specimens at high resolution. With tiling microscopes, the image of a small area of the specimen is recorded with a digital camera (usually a CCD camera), the specimen is moved with a computer-controlled microscope stage to image an adjacent area, an image of the adjacent area is recorded, the stage is moved again to the next area, and so on until a number of image tiles have been recorded that together cover the whole area of the specimen. Images of each area (image tiles) are recorded when the stage is stationary, after waiting long enough for vibrations from the moving stage to dissipate, and using an exposure time that is sufficient to record the fluorescence images. These image tiles can be butted together, or overlapped and stitched using computer stitching algorithms, to form one image of the entire specimen. Such images may contain tiling artifacts, caused by focus changes between adjacent tiles, differences in illumination intensity across the field of view of the microscope, barrel or pincushion distortion near the edge of the tiles, and microscope objectives that do not have a flat focal plane. For large specimens, thousands of tiles may be required to image the entire specimen, increasing the chance of tiling artifacts. Tiling microscopes are very slow for fluorescence imaging.

When tiling microscopes are used for fluorescence imaging, the areas surrounding each tile and the overlapping edges of adjacent tiles are exposed twice (and the corners four times) which can bleach some fluorophores. Exposure is adjusted by changing the exposure time for each tile. If multiple fluorophores are imaged, a different exposure time is required for each, so each fluorophore requires a separate image at each tile position. Multiple exposure of the specimen for imaging multiple fluorophores can also increase bleaching. After all tiles have been collected, considerable effort (both human and computer) is required to stitch the tiles together and correct each tile for illumination intensity and collection sensitivity changes across the field of view of the microscope (correction for variations in illumination intensity and collection sensitivity is sometimes called "field flattening"). Stitching tiles together is also complicated by distortion and curvature of field of the microscope objective, which occur near the edges of the field of view (just where stitching of tiles occurs).

Strip scanning instruments are also used for imaging large specimens. In these instruments infinity-corrected microscope optics are used, with a high Numerical Aperture (high NA) microscope objective and a tube lens of the appropriate focal length to focus an image of the specimen directly on a CCD or CMOS linear array sensor or TDI sensor with the correct magnification to match the resolution of the microscope objective with the detector pixel size for maximum magnification in the digitized image {as described in "Choosing Objective Lenses: The Importance of Numerical Aperture and Magnification in Digital Optical Microscopy", David W. Piston, Biol. Bull. 195, 1-4 (1998)}. A linear CCD detector array with 1000 or 2000 pixels is often used, and three separate linear detectors with appropriate filters to pass red, green and blue light are used for RGB brightfield imaging. The sample is moved at constant speed in the direction perpendicular to the long dimension of the linear detector array to scan a narrow strip across a microscope slide. The entire slide can be imaged by imaging repeated strips and butting them together to create the final image. Another version of this technology uses linear TDI (Time Delay Integration) array sensors which increase both sensitivity and imaging speed. In both of these instruments, exposure is varied by changing illumination intensity and/or scan speed.

Such a microscope is shown in FIG. 1 (Prior Art). A tissue specimen 100 (or other specimen to be imaged) mounted on microscope slide 101 is illuminated from below by illumination source 110. Light passing through the specimen is collected by infinity-corrected microscope objective 115, which is focused on the specimen by piezo positioner 120. The microscope objective 115 and tube lens 125 form a real image of the specimen on linear detector array 130. An image of the specimen is collected by moving the microscope slide at constant speed using motorized stage 105 in a direction perpendicular to the long dimension of the detector array 130, combining a sequence of equally-spaced line images from the array to construct an image of one strip across the specimen. Strips are then assembled to form a complete image of the specimen.

For brightfield imaging, most strip-scanning instruments illuminate the specimen from below, and detect the image in transmission using a sensor placed above the specimen. In brightfield, signal strength is high, and red, green and blue channels are often detected simultaneously with separate linear detector arrays to produce a colour image.

Compared to brightfield imaging, fluorescence signals can be thousands of times weaker, and some fluorophores have much weaker emission than others. Fluorescence microscopy is usually performed using illumination from the same side as detection (epifluorescence) so that the bright illumination light passing through the specimen does not enter the detector. In strip-scanning instruments, exposure is varied by changing scan speed, so present strip-scanning instruments scan each fluorophore separately, reducing the scan speed when greater exposure is required for a weak fluorophore. Varying exposure by changing scan speed makes it difficult to design a strip-scanner for simultaneous imaging of multiple fluorophores, where each channel would have the same exposure time, and present strip-scanners scan one fluorophore at-a-time. In addition, in fluorescence microscopy, relative intensity measurements are sometimes important for quantitative measurement, and 12 or 16 bit dynamic range may be required. For present strip scanners, this would require larger dynamic range detectors and slower scan speeds.

Before scanning a large specimen in fluorescence, it is important to set the exposure time (in a tiling or strip-scanning microscope) or the combination of laser intensity, detector gain and scan speed (in a scanning laser macroscope or microscope) so that the final image will be properly exposed—in general it should not contain saturated pixels, but the gain should be high enough that the full dynamic range will be used for each fluorophore in the final image. Two problems must be solved to achieve this result—the exposure must be estimated in advance for each fluorophore and for simultaneous detection of multiple fluorophores, the exposure time must be adjusted separately for each detection channel before scanning. For strip-scanning instruments, estimating the exposure in advance is difficult without scanning the whole specimen first to check exposure, and this must be done for each fluorophore. Instead of scanning first to set exposure, many operators simply set the scan speed to underexpose slightly, with resulting noisy images, or possibly images with some overexposed (saturated) areas if the estimated exposure was not correct. For macroscope-based instruments, a high-speed preview scan can be used to set detection gain in each channel before final simultaneous imaging of multiple fluorophores (see WO2009/137935, "Imaging System with Dynamic Range Maximization").

A prior art scanning microscope for fluorescence imaging is shown in FIG. 2. A tissue specimen 100 (or other specimen to be imaged) mounted on microscope slide 101 is illuminated from above by illumination source 200. In fluorescence imaging the illumination source is usually mounted above the specimen (epifluorescence) so that the intense illumination light that passes through the specimen is not mixed with the weaker fluorescence emission from the specimen, as it would be if the illumination source were below the specimen. Several different optical combinations can be used for epifluorescence illumination—including illumination light that is injected into the microscope tube between the microscope objective and the tube lens, using a dichroic beamsplitter to reflect it down through the microscope objective and onto the specimen. In addition, a narrow wavelength band for the illumination light is chosen to match the absorption peak of the fluorophore in use. Fluorescence emitted by the specimen is collected by the infinity-corrected microscope objective 115 which is focused on the specimen by the piezo positioner 120. Emission filter 205 is chosen to reject light at the illumination wavelength and to pass the emission band of the fluorophore in use. The microscope objective 115 and the tube lens 125 form a real image of the specimen on TDI detector array 210. An image of the specimen is collected by moving the microscope slide at constant speed using the motorized stage 105 in a direction perpendicular to the long dimension of the detector array 210, combining a sequence of equally-spaced, time-integrated line images from the array to construct an image of one strip across the specimen. Strips are then assembled to form a complete image of the specimen. When a CCD-based TDI array is used, each line image stored in memory is the result of integrating the charge generated in all of the previous lines of the array while the scan proceeds, and thus has both increased signal/noise and amplitude (due to increased exposure time) when compared to the result from a linear array detector. Exposure is also increased by reducing scan speed, so the scan time (and thus image acquisition time) is increased when using weak fluorophores. In addition, it is difficult to predict the best exposure time before scanning. When multiple fluorophores are used on the same specimen, the usual imaging method is to choose illumination wavelengths to match one fluorophore, select the appropriate emission filter and scan time (speed) for the chosen fluorophore, and scan one strip in the image. Then, the illumination wavelength band is adjusted to match the absorption band of the second fluorophore, a matching emission filter and scan speed are chosen, and that strip is scanned again. Additional fluorophores require the same steps to be repeated. Finally, this is repeated for all strips in the final image. Some instruments use multiple TDI detector arrays to expose and scan multiple fluorophores simultaneously, but this usually results in a final image where one fluorophore is exposed correctly and the others are either under- or over-exposed. Exposure can be adjusted by changing the relative intensity of the excitation illumination for each fluorophore, which should be easy to do if LED illumination is used. When multiple illumination bands are used at the same time, the resulting image for each fluorophore may differ from that produced when only one illumination band is used at a time because of overlap of the fluorophore emission bands, and because autofluorescence from the tissue itself may be excited by one of the illumination bands. Autofluorescence emission usually covers a wide spectrum and may cause a bright background in all of the images when multiple fluorophores are illuminated and imaged simultaneously.

A good description of strip scanning instruments, using either linear arrays or TDI arrays, is given in US Patent Application Publication No. US2009/0141126 ("Fully Automatic Rapid Microscope Slide Scanner", by Dirk Soenksen).

Linear arrays work well for brightfield imaging, but the user is often required to perform a focus measurement at several places on the specimen before scanning, or a separate detector is used for automatic focus. Linear arrays are not often used for fluorescence imaging because exposure time is inversely proportional to scan speed, which makes the scan time very long for weak fluorophores. In addition, exposure (scan speed) must be adjusted for each fluorophore, making simultaneous measurement of multiple fluorophores difficult when they have widely different fluorescence intensity (which is common).

TDI arrays and associated electronics are expensive, but the on-chip integration of several exposures of the same line on the specimen provides the increased exposure time required for fluorescence imaging while maintaining a reasonable scan speed. Simultaneous imaging of multiple fluorophores using multiple TDI detector arrays is still very difficult however, since each of the detectors has the same integration time (set by the scan speed), so it is common to use only one TDI array, adjusting exposure for each fluorophore by changing the scan speed and collecting a separate image for each fluorophore. Focus is set before scanning at several positions on the specimen, or automatic focus is achieved using a separate detector or focus measuring device.

Single-chip colour cameras (including those often used on ordinary optical microscopes to record an image of the specimen area seen in the field of view of the microscope) often use a mosaic Colour Filter Array (CFA) on the photosensors of an area detector that enables a single-chip camera to record a colour image. The most common CFA is the Bayer filter, named after the inventor, which arranges red, green and blue filters in a square grid (usually RGGB) of photosensors on the array (see U.S. Pat. No. 3,971,065). Bayer chose to use two green pixels in each set as luminance elements to match the sensitivity of the human eye. Data from each pixel only records one colour, so in order to obtain a full-colour image, the red, green and blue values for each pixel are calculated by interpolation using information from the surrounding pixels. This is called demosaicing, and several different demosaicing algorithms have been developed. Demosaicing may happen inside the camera (producing jpeg or tiff files), or outside using raw data from the sensor. Because of the computing power required for demosiacing, and the possibility of false colours and moiré, most tiling microscopes use separate array detectors to detect red, green and blue. Cameras for digital photography often use an optical low-pass filter in front of the detector array to reduce moiré and false colour caused by use of a Bayer filter, resulting in some loss of resolution. Other mosaic Colour Filter Arrays have been proposed, including one using a white (transparent) filter in place of one of the green filters in the Bayer array. White (transparent) pixels accept all wavelengths of light in the visible spectrum (they are panchromatic), and provide one bright pixel in each array of four pixels, increasing the sensitivity of the array. Other combinations of filters in the square mosaic grid include CYGM (cyan, yellow, green, magenta) and RGBE (red, green, blue, emerald). All require demosaicing.

DEFINITIONS AND OBJECTS OF THE INVENTION

For the purposes of this patent document, a "macroscopic specimen" (or "large microscope specimen") is defined as one that is larger than the field of view of a compound optical microscope containing a microscope objective that has the same Numerical Aperture (NA) as that of the scanner described in this document.

For the purposes of this patent document, TDI or Time Delay and Integration is defined as the method and detectors used for scanning moving objects, usually consisting of a CCD-based detector array in which charge is transferred from one row of pixels in the detector array to the next in synchronism with the motion of the real image of the moving object. As the object moves, charge builds up and the result is charge integration just as if a longer exposure was used in a stationary imaging situation. When the image (and integrated charge) reaches the last row of the array, that line of pixels is read out. In operation the last line of the moving image is read out continuously, one row of pixels at a time. One example of such a camera is the DALSA Piranha TDI camera.

For the purposes of this patent document the term "image acquisition" includes all of the steps necessary to acquire and produce the final image of the specimen, including some of but not limited to the following: the steps of preview scanning, instrument focus, predicting and setting gain for imaging each fluorophore, image adjustments including scan linearity adjustment, field flattening (compensating for fluorescence intensity variation caused by excitation intensity and detection sensitivity changes across the field of view), correction of fluorescence signal in one channel caused by overlap of fluorescence from adjacent (in wavelength) channels when two or more fluorophores are excited simultaneously, dynamic range adjustment, butting or stitching together adjacent image strips (when necessary), storing, transmitting and viewing the final image.

For the purposes of this patent document, the term "image processing" means all of the steps required to process the data to prepare the final image file, including some of but not limited to the following: the steps of scan linearity adjustment, field flattening, correction for crosstalk when simultaneously scanning multiple fluorophores, correcting fluorescence image data by subtracting fluorescence originating from the glass of the microscope slide, subtracting the dark-current noise floor from the detector, and contracting the dynamic range of the image data to match the (smaller) dynamic range of the final image.

"Proper exposure" is defined as a gain setting such that in the output image file no (or only a small number of) pixels are saturated, and the dynamic range of the image data matches the dynamic range of the output image file (8 bits for an 8 bit file, 12 bits for a 12 bit file, etc.) and includes substantially the entire range of pixel amplitudes from the noise floor to the brightest pixel. The output image file may have a smaller dynamic range than that of the detection system, and that of an intermediate image file that is collected during scanning. WO2009/137935 describes two methods of maximizing the dynamic range of data stored in the output image file—(1) accurately estimating the gain required to maximize the dynamic range of each detection channel when the dynamic range of the detection channel and the dynamic range of the output image data file are the same, and (2) using a dynamic range in the detection channel that is larger than that required in the final image data file and contracting the acquired data to utilize substantially the entire dynamic range of the final image data file.

For the purposes of this patent document, the term "sparse image" means an image in which only pixels in a sparse grid exist in the image—e.g. one pixel at the centre of a square area of the image that would normally contain 100 or more pixels. The pixel values (intensities) are the same as they would be in the complete image, and do not reflect in any way the values of the pixels that were discarded (or not measured) to produce the sparse image.

For the purposes of this patent document, a "frame grabber" is any electronic device that captures individual, digital still frames from an analog video signal or a digital video stream or digital camera. It is often employed as a component of a computer vision system, in which video frames are captured in digital form and then displayed, stored or transmitted in raw or compressed digital form. This definition includes direct camera connections via USB, Ethernet, IEEE 1394 ("FireWire") and other interfaces that are now practical.

Objects of the Invention

It is an object of this invention to provide a method of using a CCD or CMOS or other technology two-dimensional sensor array for imaging moving objects instead of using linear array or TDI (time delay and integration) line scan technology.

It is an object of this invention to provide an instrument and method of scanning large microscope specimens on a moving microscope stage using one or more CCD or CMOS or other technology two-dimensional sensor arrays in place of linear arrays or TDI arrays.

It is an object of this invention to provide an imaging system for large microscope specimens using one or more CCD or CMOS or other technology two-dimensional sensor arrays whereby noise in the image is reduced by adding together a sequence of overlapping images on a line-by-line basis, whereby each line of the final image is the result of adding several exposures of the same line, thus increasing the exposure time for that line in the image.

(Each line in the final image is the result of adding several exposures of the same line and then dividing by the number of exposures, or adding the data from each exposure to a data set with a larger dynamic range, e.g. one could add 256 images from an 8-bit detector into a 16-bit image store). (Then, dynamic-range contraction can be used on each fluorophore image to fill the dynamic range required in the output file for each fluorophore, as described in WO2009/137935).

It is an object of this invention to provide a method of scanning large microscope specimens on a moving microscope stage using one or more CCD or CMOS or other technology two-dimensional sensor arrays in place of linear arrays or TDI arrays that allows simultaneous imaging of multiple fluorophores, even where there is a large difference in the signal strength of the different fluorophores. {For example, consider an 8-bit sensor array (or an array in which the 8 most-significant bits are commonly read out) and a 16-bit image store for each fluorescence detection channel. Up to 256 8-bit measurements can be added to each pixel in the 16-bit image store, and, if desired, the resulting 16-bit image can be contracted back to 8 bits, using the contraction methods described in WO2009/137935. Contraction can be different for each fluorescence channel so that the resulting 8-bit image from each channel fills the 8 bit dynamic range commonly available for viewing each colour.}

It is an object of this invention to provide a fluorescence imaging system for large microscope specimens using CCD or CMOS or other technology two-dimensional sensor arrays in place of linear arrays or TDI arrays whereby the dynamic range of the instrument is larger than the dynamic range of the detector. (e.g. using an 8-bit detector, adding together 256 8-bit images results in a final image with a dynamic range of 16 bits)

It is an object of this invention to provide a fluorescence imaging system for detecting multiple fluorophores in large microscope specimens using CCD or CMOS or other technology two-dimensional sensor arrays in place of linear arrays or TDI arrays whereby the dynamic range of the acquired data in each of the separate fluorescence images (one from each fluorophore) can be contracted to fill (or substantially fill) the entire dynamic range of the output image data file for each fluorophore. (See WO2009/137935 for examples of image data dynamic range contraction.)

It is an object of this invention using CCD or CMOS or other technology two-dimensional sensor arrays in place of linear arrays or TDI arrays to provide a method of acquiring fluorescence images in which the image data from each fluorophore substantially fills the dynamic range available in the final image file, by estimating the gain required to maximize the dynamic range for each fluorophore in a fluorescence image before scanning, using detection channels that have larger dynamic range than that required in the final image, and contracting the dynamic range of the acquired data to fill substantially the entire dynamic range of the output image data file for each fluorophore.

It is an object of this invention using CCD or CMOS or other technology two-dimensional sensor arrays in place of linear arrays or TDI arrays to provide a fluorescence imaging system for macroscopic specimens in which the correct gain setting for fluorescence imaging can be estimated from a preview scan of the entire specimen (or part of the specimen) before the final scan is started. (For example, using a sparse pixel image from a high-speed preview scan)

It is an object of this invention using CCD or CMOS or other technology two-dimensional sensor arrays in place of linear arrays or TDI arrays to provide a fluorescence imaging system for macroscopic specimens in which the correct gain setting for each fluorophore detection channel when simultaneously imaging multiple fluorophores can be estimated from a preview scan of the entire specimen (or part of the specimen) before the final scan is started. (e.g. Sparse pixel images from each detection channel)

It is an object of this invention to provide an imaging system for imaging specimens containing fluorescent nanoparticles using CCD or CMOS or other technology two-dimensional sensor arrays in place of linear arrays or TDI arrays in which the correct gain setting for fluorescence imaging can be estimated from a preview scan of the entire specimen (or part of the specimen) before the final scan is started.

It is an object of this invention using CCD or CMOS or other technology two-dimensional sensor arrays in place of linear arrays or TDI arrays to provide a method of using the data stored in the image histogram during scanning to contract the dynamic range of the image data file after scanning is complete, and to provide a method of performing such contraction either manually or automatically on the stored images of scan strips before the final image is assembled. This operation can be performed in the background while scanning of the next strip is underway (but all strips must be contracted equally).

It is an object of this invention using CCD or CMOS or other technology two-dimensional sensor arrays in place of linear arrays or TDI arrays to provide a method of using the preview image histogram to provide a method of performing dynamic range contraction and other image processing operations on the data stream during scan, such that the image being stored during scan has already been contracted to the dynamic range required in the output image file, and required image processing operations have been completed during scan.

It is an object of this invention using CCD or CMOS or other technology two-dimensional sensor arrays in place of linear arrays or TDI arrays to provide a means and method for fluorescence imaging of genetic, protein or tissue microarrays.

It is an object of this invention using CCD or CMOS or other technology two-dimensional sensor arrays in place of linear arrays or TDI arrays to provide a means and method for fluorescence imaging of microarrays, in which the correct gain setting and dark current offset can be estimated from a high-speed preview scan of the entire specimen or part of the specimen.

It is an object of this invention using CCD or CMOS or other technology two-dimensional sensor arrays in place of linear arrays or TDI arrays and the scanning microscope described in FIG. 3 or FIG. 7 to provide a means and method for acquiring an image of the entire specimen which can be used as an index image, followed by acquisition of single field-of-view images at one or several positions on the specimen, where such single field-of-view images are acquired while the stage is stationary. These single field-of-view images can be either brightfield or fluorescence, and allow the operator to view changes in the specimen as a function of time. Video-rate acquisition enables these changes to be viewed in real time. Increased exposure of single field-of-view fluorescence images can be accomplished by increasing the time the shutter is open, or by adding a series of images of the same field-of-view (which also allows the dynamic range in the image to be larger than that of the detector array). Increased optical resolution can be achieved in the single field-of-view images using structured illumination (see "Widefield fluorescence microscopy with extended resolution" by A Stemmer, M Beck & R Fiolka, Histochem Cell Biol 130 (807-817) 2008). Optical sectioning can be accomplished in the single field-of-view images by injecting a laser beam into the tube of the microscope through a diffuser plate, which is imaged onto the back aperture of the objective (or by simply illuminating the specimen directly). Two images can be acquired, one illuminated by speckle when the diffuser plate is stationary, and a second uniform-illumination image when the diffuser plate is in rapid motion. These two images can be processed and combined to give a final optically-sectioned high resolution image, as described in "Wide-field fluorescence sectioning with hybrid speckle and uniform-illumination microscopy" by D. Lim, K. Chu & J. Mertz, Optics Letters 33 (1819-1821) 2008.

It is an object of this invention using CCD or CMOS or other technology two-dimensional sensor arrays to provide a slide-scanner instrument and method for brightfield imaging of large specimens mounted on microscope slides using a single two-dimensional sensor array in which the array is divided into thirds, with one third covered with a red transmission filter, one with a green transmission filter, and one with a blue transmission filter, in which each third of the detector acquires a strip image and the three images can be combined digitally to produce an RGB brightfield image.

It is an object of this invention using CCD or CMOS or other technology two-dimensional sensor arrays to provide a slide scanner instrument and method for fluorescence imaging of large specimens containing multiple fluorescent dyes or other sources of fluorescence mounted on microscope slides using a single two-dimensional sensor array in which the array is divided into fractions, one for each fluorescent source, with each section covered with a transmission filter that transmits the emission peak of one of the fluorescent dyes or sources, in which each fraction of the detector acquires a strip image and the multiple strip images can be combined digitally to produce a single fluorescence image (which may be presented as a false colour image) or each image can be viewed separately.

It is an object of this invention using CCD or CMOS or other technology two-dimensional sensor arrays and a tunable filter to provide a multi-spectral fluorescence slide scanner and method for imaging large specimens mounted on microscope slides.

It is an object of this invention to provide an instrument and method for brightfield scanning using a two-dimensional sensor array that uses a Bayer filter (or other filter using a mosaic square grid array) that does not require demosaicing.

It is an object of this invention to provide an instrument and method for scanning a specimen on a microscope slide containing multiple fluorophores in a single scan, using a two-dimensional sensor array and Moving Specimen Image Averaging in which changes in the excitation and emission wavelengths are synchronized together and with the motion of the specimen stage.

It is an object of this invention to provide new designs for Colour Filter Arrays that are optimized for use with Moving Specimen Image Averaging, do not require demosaicing, and can be used for brightfield and/or fluorescence imaging.

It is an object of this invention to provide a colour camera and method for brightfield MSIA imaging.

It is an object of this invention to provide a camera and method for brightfield and/or fluorescence imaging using MSIA.

SUMMARY OF THE INVENTION

A scanning microscope for obtaining a final contiguous colour image of at least a portion of a specimen, the microscope comprising:

a) an illumination system to illuminate a part of the specimen being scanned;

b) at least one lens that focuses light from the specimen onto a two dimensional sensor array, the specimen mounted on a support that is movable relative to the two dimensional sensor array;

c) the two dimensional sensor array having a plurality of rows and columns, and having a colour filter array, the colour filter array that is one selected from the group of:
   (i) a mosaic colour filter; and
   (ii) a scanning colour filter array having a plurality of at least XN rows with each row being one colour, N being the number of adjacent rows of the same colour and being equal to or greater than one, X being the number of different colours and being equal to or greater than three, the XN rows forming a pattern, a sequence of the pattern being repeated as required to cover the entire sensor array, the scanning colour filter array having a plurality of rows of each colour;

d) the sensor array having a shutter, the shutter synchronized to open, acquire multiple two dimensional image frames of the specimen and close with the motion of the specimen relative to each line of the sensor array each time that an optical image of the specimen has moved a distance that is equal to the distance between adjacent rows of the sensor array, the sensor array acquiring image frames when the shutter is open and data for the image frames acquired being transferred to a frame capture device when the shutter is closed, the sensor array acquiring multiple image frames of the specimen in one or more image strips, there is one image strip for each colour, each image frame comprising a plurality of adjacent lines of the sensor array and immediately adjacent image frame each shifted from one another by one line of the sensor array, the sensor array acquiring a two dimensional image frame of the specimen each time that the shutter opens and closes;

e) each image strip having a width equal to a width respectively of the colour filter array, the colour filter array having a length and width corresponding to the length and width respectively of the sensor array;

f) a processor programmed:

(i) to receive data for all image frames acquired, as the opening and closing of the shutter is repeated numerous times the data for newly acquired mage frames is averaged with or added to the data already stored each time creating a lengthening strip image of one of the one or more image strips, the data for all image frames acquired and the image strips are created simultaneously for each image strip and the image frames are accessible to the processor as the data is acquired;

(ii) to assemble all of the image strips acquired; and (iii) to average adjacent nearest pixel values of the same colour when required to produce full colour information at each pixel position in the strip image and to create and store a final contiguous colour image of the portion of the specimen scanned, the final image containing full colour information at each image pixel position for each colour of the colour filter array.

A scanning microscope for scanning and obtaining a colour image of at least a portion of a specimen, the microscope comprising:

a) an illumination system to illuminate a part of the specimen being scanned, b) at least one lens that focuses light from the specimen onto a two dimensional sensor array, the specimen being mounted on a support that is movable relative to the two dimensional sensor array, c) the two dimensional sensor array having a colour filter array and a shutter, the shutter synchronized to open, acquire multiple image frames in one image strip for each colour of each area of the specimen being scanned through the colour filter array for a plurality of adjacent lines of the sensor array and close as the specimen moves continuously line by line relative to the sensor array, each image comprising a plurality of adjacent lines of the sensor array immediately adjacent images each shifted from one another by one line of the sensor array, d) a processor programmed to receive data for all image frames acquired for each of the image strips from the sensor array each time that the shutter of the sensor array opens and closes, each time that the shutter closes image data from newly acquired images is averaged with or added to the data already stored creating a lengthening strip image of the one or more image strips, the processor programmed to average adjacent nearest pixel values of the same colour when required to produce full colour information at each pixel position in the strip image and to create and store a final contiguous colour image of the portion of the specimen scanned, the final image containing full colour information at each image pixel position for each colour of the colour filter array.

A scanning colour filter array comprises a plurality of rows where all detector pixels in each row have the same colour, but the colour differs between adjacent rows. The filter array has at least eight rows, at least two rows of which contain white detector pixels, at least two rows of which contain red detector pixels, at least two rows of which contain green detector pixels and at least two rows of which contain blue detector pixels. A pattern of colours repeating every four rows, the colour filter array being optimized for Moving Specimen Imaging Averaging by which an instrument acquiring images of an area of a specimen as the specimen moves line by line relative to a two dimensional sensor array. The two dimensional sensor array has a shutter synchronized to open, acquire multiple images in one image strip for each colour of each area of the specimen being scanned through the scanning colour filter array for a plurality of lines of the sensor array and close. A processor is programmed to receive data for the images from each of the image strips from the sensor array each time that the shutter of the sensor array opens and closes. The processor is programmed to add to the data already stored the data for newly acquired images each time that the shutter closes, thereby creating a lengthening strip image of the one or more image strips. The processor is further programmed to produce a final contiguous colour image from all of the image strips, the final image containing full colour information at each image pixel position for each colour of the filter array.

A method of scanning a specimen using a scanning microscope has a light source and an optical train has at least one lens to focus light from the specimen onto a two dimensional sensor array. The specimen is mounted on a support that is movable relative to the two dimensional sensor array. The method comprises using a mosaic colour filter array with the two dimensional sensor array, the sensor array having a shutter and moving the specimen and specimen support line by line relative to the sensor array while scanning the specimen and synchronizing the shutter to open, acquire multiple images in one image strip for each colour of each area of the specimen being scanned for a plurality of lines of the sensor array and close as the specimen moves line by line relative to the sensor array, there being a plurality of image strips, each image comprising a plurality of adjacent lines of the sensor array and immediately adjacent images each shifted from one another by one line of the sensor array, the sensor array acquiring a two dimensional image each time that the shutter opens and closes, and programming a computer to receive data for the images from each of the image strips from the sensor array each time that a shutter of the sensor array opens and closes, programming the processor to average with or add to the data already stored the data for newly acquired images each time that the shutter closes, thereby creating a lengthening strip image of the one or more image strips, the programming the processor to average adjacent nearest pixel values of the same colour when required to produce full colour information at each pixel position in the strip image and to create and store a final contiguous colour image of the portion of the specimen scanned, the final image containing full colour information at each image pixel position for each colour of the colour filter array to calculate full colour values at each image pixel position on the image strip for that colour by interpolating measured values for that colour at adjacent image pixel positions and adding the interpolated values to the image strip corresponding to that colour, and further programming the processor to assemble all of the image strips acquired to produce a final contiguous colour image.

A method of scanning a specimen using a scanning microscope has a light source and an optical train has at least one lens to focus light from the specimen onto a two-dimensional sensor array. The specimen is mounted on a support that is movable relative to the sensor array. The method comprises using a scanning colour filter array on the two dimensional sensor array, the sensor array having a shutter and moving the specimen and specimen support line by line relative to the sensor array during scanning and synchronizing the shutter to open, acquire multiple images in one image strip for each colour of each area of the specimen being scanned for a plurality of lines of the sensor array and close, there being a plurality of image strips, each image comprising a plurality of adjacent lines of the sensor array and immediately adjacent images each shifted from one another by one line of the sensor array, the sensor array acquiring a two dimensional image each time that the shutter opens and closes, and programming a computer to receive data for the images from each of the image strips from the sensor array each time that a shutter of the sensor array opens and closes, the computer programmed to add to the data already stored, the data for newly acquired images each time that the shutter closes, thereby creating a lengthening strip image of the one or more image strips, programming the computer to access the acquired images to provide full colour information at each image pixel position and further programming the computer to assemble all of the image strips acquired to produce a final contiguous colour image, of the specimen scanned, the final image containing full colour information at each image pixel position for each colour of the colour filter array.

A scanning colour filter array comprises a plurality of rows where all pixels in each row have the same colour, but the colour differs between adjacent rows. There are at least three rows of different colours, a colour sequence of the at least three rows being repeated at least once in additional rows of the scanning colour filter array by which an instrument acquires multiple images in one or more image strips of a specimen as the specimen moves line by line relative to a two dimensional sensor array. The sensor array has a shutter synchronized to open, acquire an image of each area of the specimen being scanned for a plurality of lines of the sensor array and close. Each image comprises a plurality of adjacent lines of the sensor array and immediately adjacent images are each shifted from one another by one line of the sensor array. The sensor array acquires a two dimensional image each time that the shutter opens and closes, and a processor is programmed to acquire data for the images in each image strip from the sensor array each time that a shutter of the sensor array opens and closes. The processor is programmed to add to the data already stored, the data for newly acquired images each time that the shutter closes, thereby creating a lengthening strip image of the one or mage image strips, and to assemble all of the image strips to produce a final contiguous colour image, of the specimen scanned, the final image containing full colour information at each image pixel position for each colour of the colour filter array.

BRIEF DESCRIPTION OF THE DIAGRAMS

Top—the entire image is read out one pixel at-a-time which is common in area arrays.

Bottom—all lines in the array are transferred out in parallel directly to lines in the image store.

Figure 7:
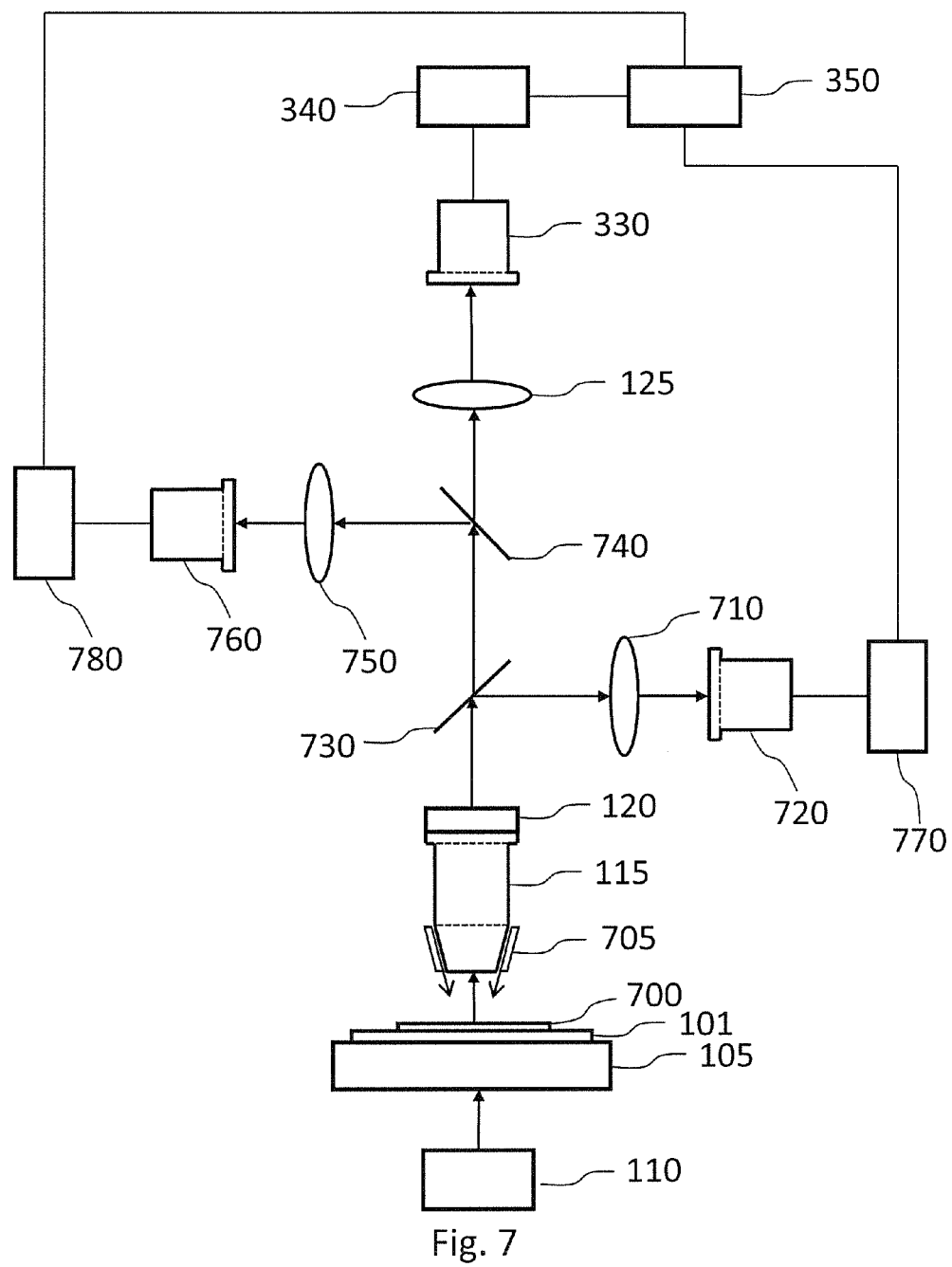

FIG. 7 shows a microscope slide scanner using area detector arrays and multiple detection arms for simultaneous detection of three fluorophores.

Figure 8:
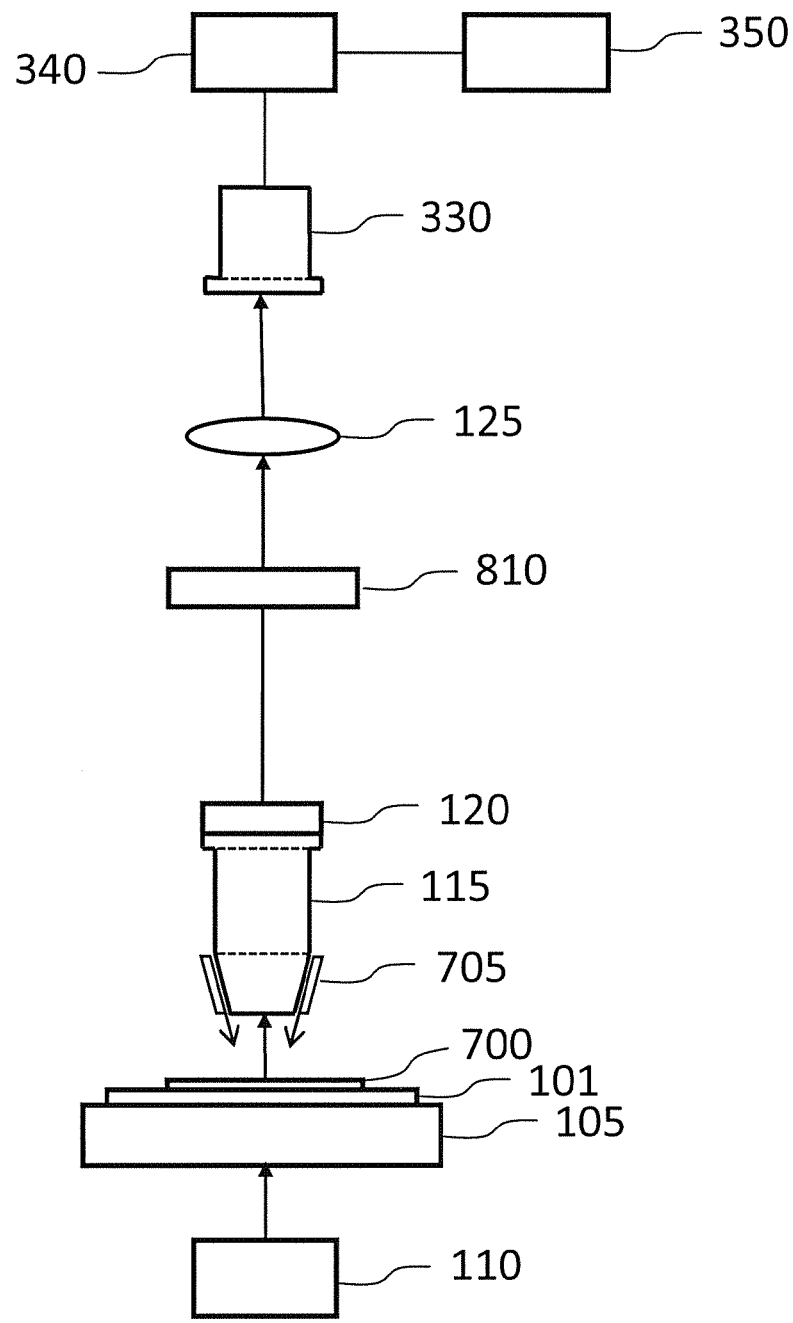

FIG. 8 shows a microscope slide scanner using a tunable filter to select the wavelength band for recording either brightfield or fluorescence images, where each colour image is recorded in sequence.

Figure 9:
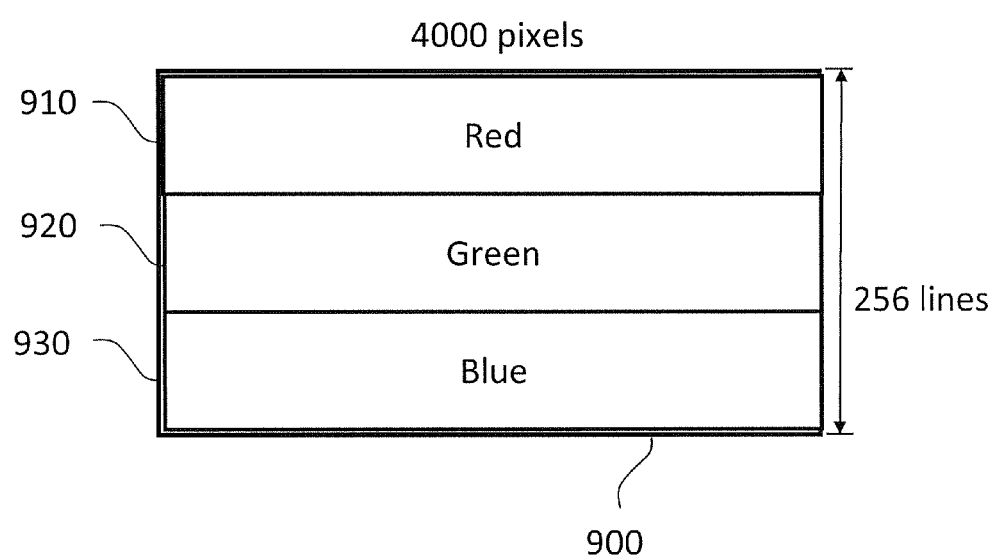

FIG. 9 shows a detector array for simultaneous imaging of three colours by covering fractions of the detector with filters that pass red, green or blue light to the three areas of the detector array.

Figure 10:
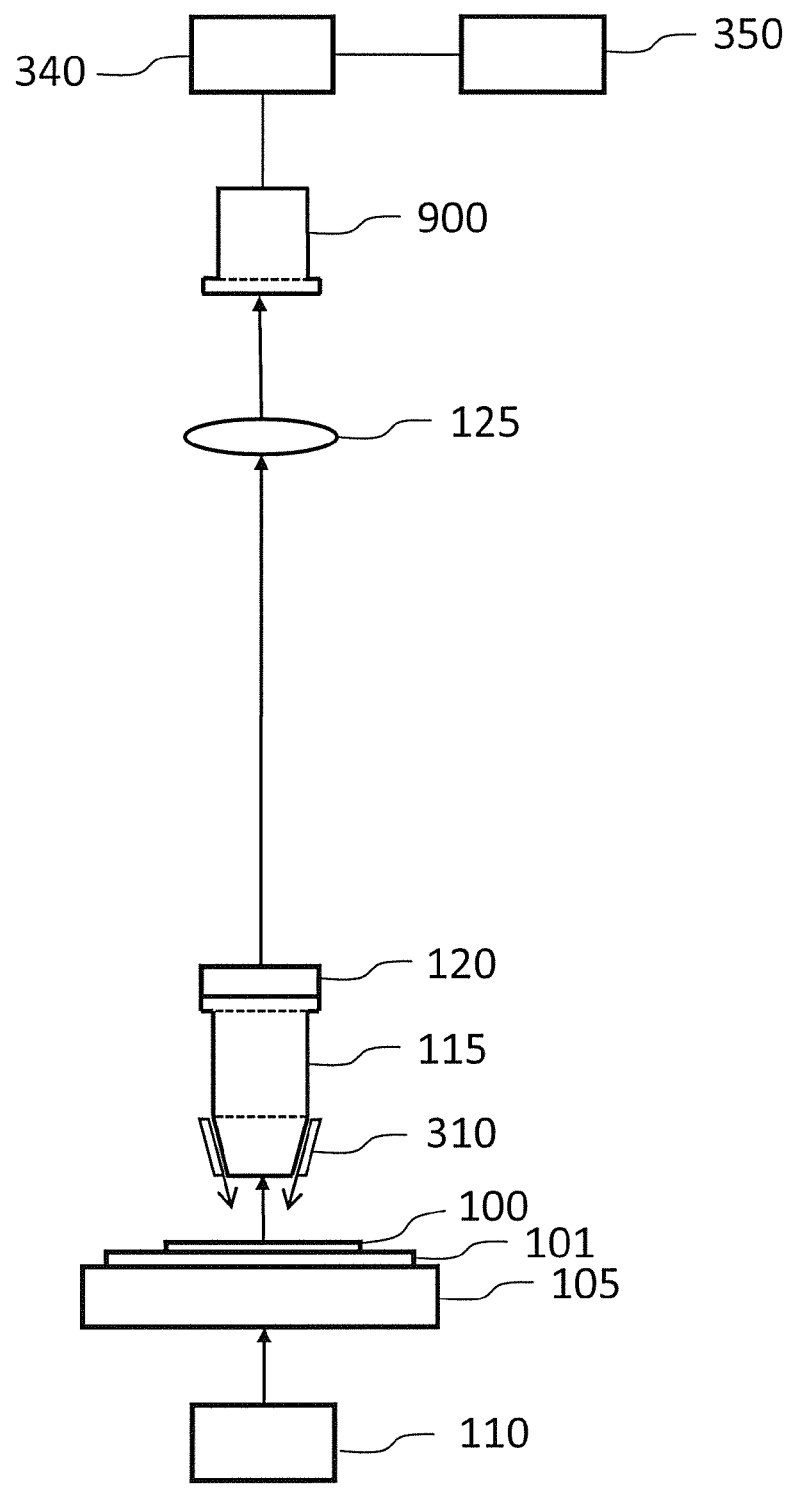

FIG. 10 shows a microscope slide scanner that uses a detector array with multiple strips of coloured transmission filters to record simultaneous images of brightfield or multiple fluorescence sources.

Figure 11:
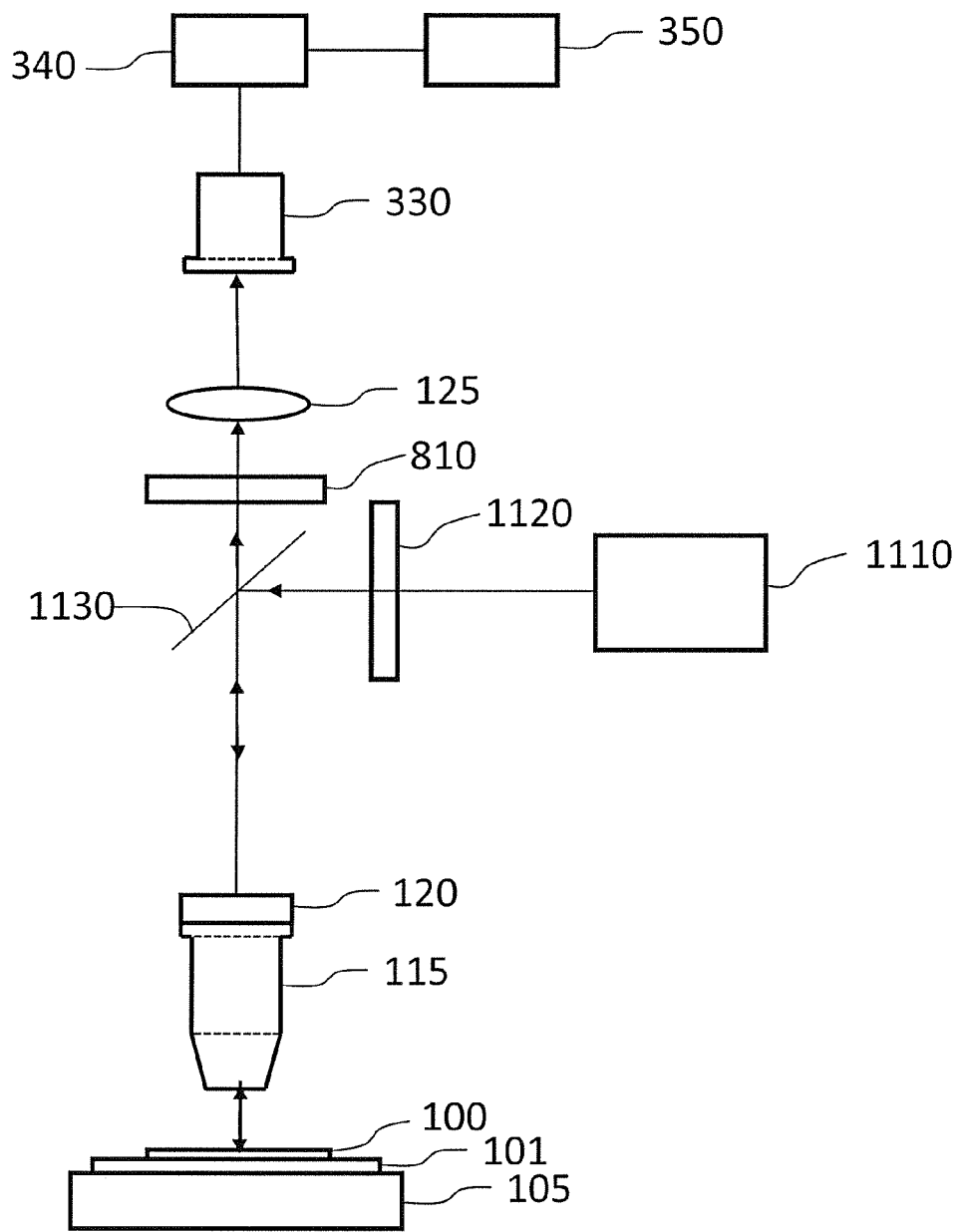

FIG. 11 shows a microscope slide scanner for fluorescence imaging in which changes in excitation and emission wavelengths are synchronized together, and with the motion of a scanning specimen stage, allowing multiple fluorophores to be detected in a single scan.

Figure 12:
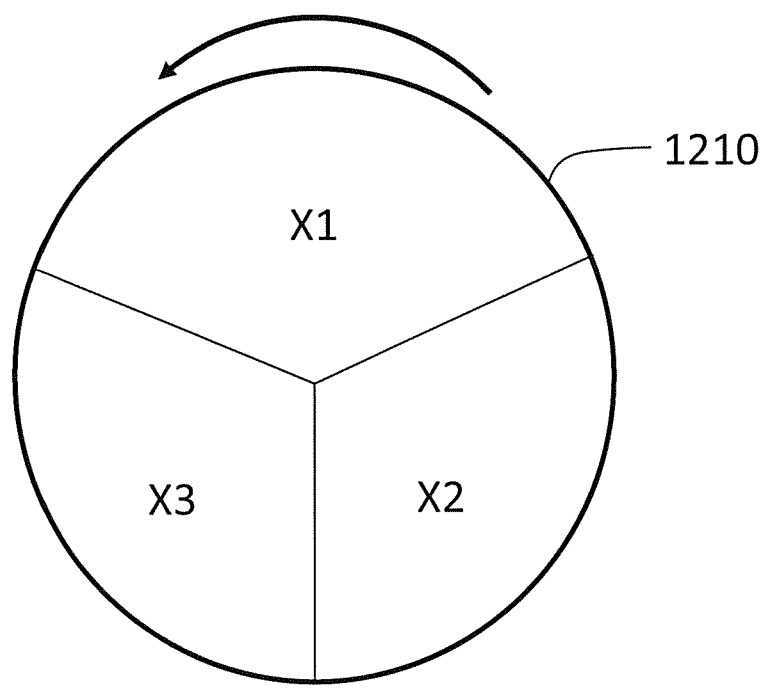
Figure 12:
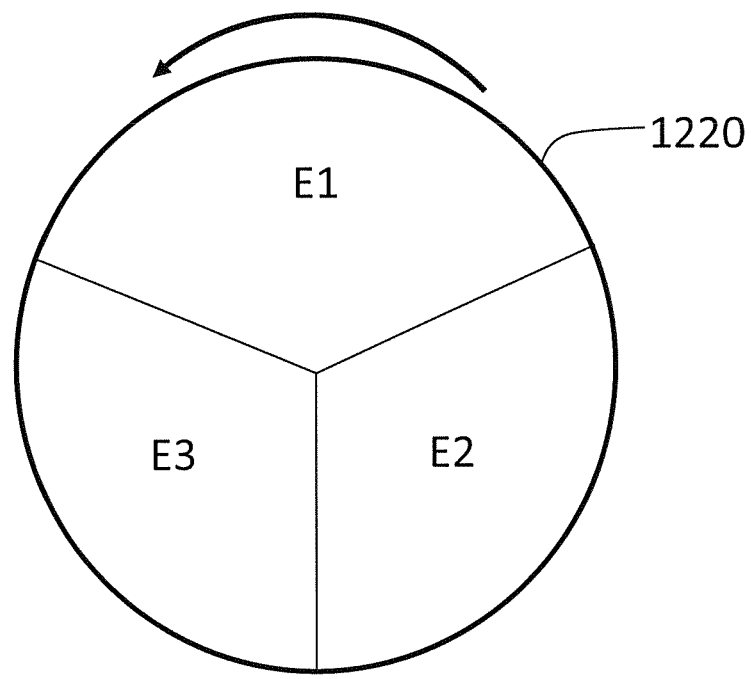

FIG. 12 shows a pair of rotating excitation and emission filters for fluorescence imaging.

Figure 13:
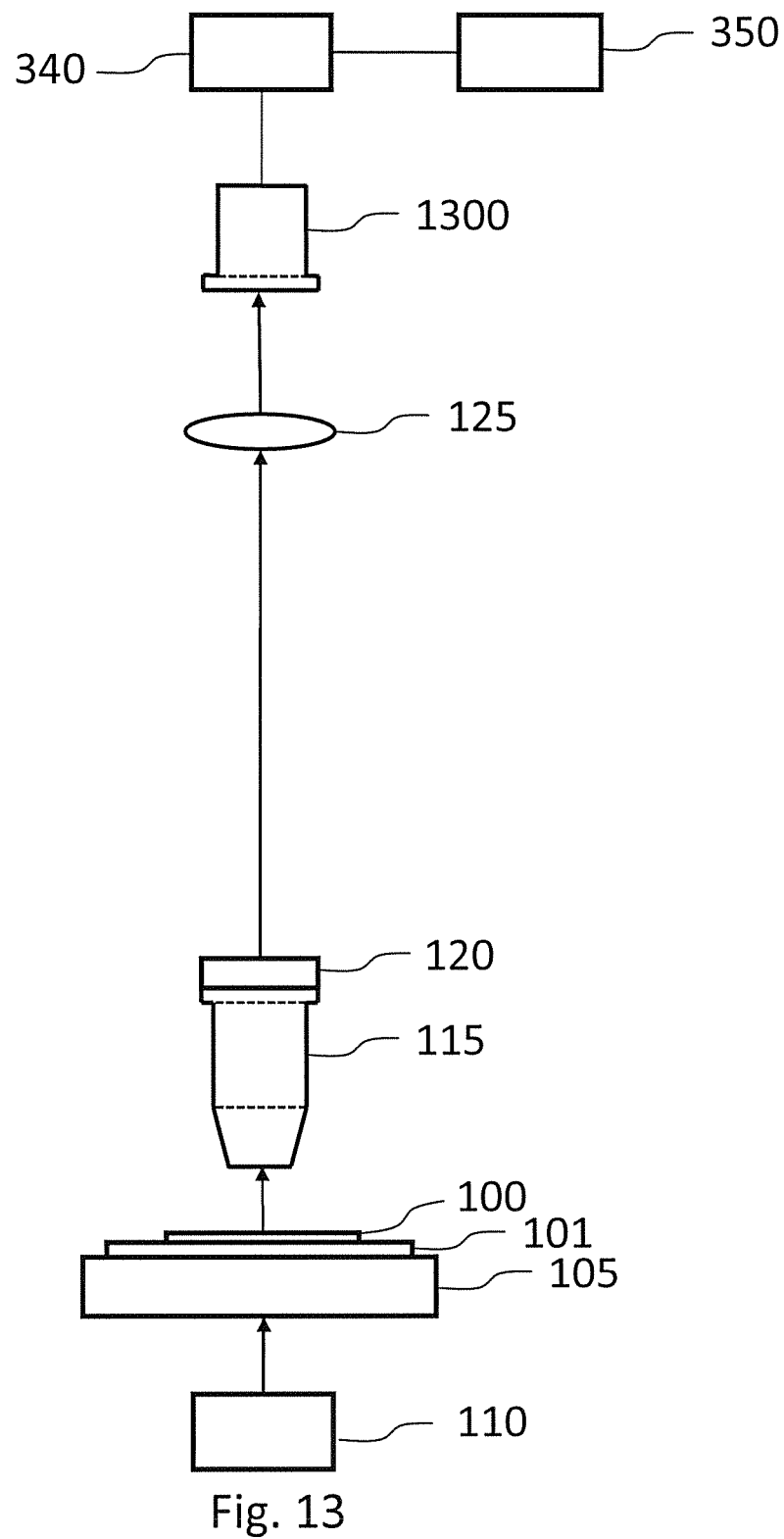

FIG. 13 shows a microscope slide scanner using an area detector array that includes a Bayer Colour Filter Array.

FIG. 14a shows the data flow in a microscope scanner using MSIA with a detector using a Bayer filter array, for the first and second exposures in a sequence.

FIG. 14b shows the data flow in a microscope scanner using MSIA with a detector using a Bayer filter array, for the third and fourth exposures in a sequence.

FIG. 14c shows the data flow in a microscope scanner using MSIA with a detector using a Bayer filter array, for the fifth exposure in a sequence.

FIG. 15 shows an RGB Colour Scan Filter Array designed for scanning moving specimens, and the data flow for two sequential exposures.

Figure 16:
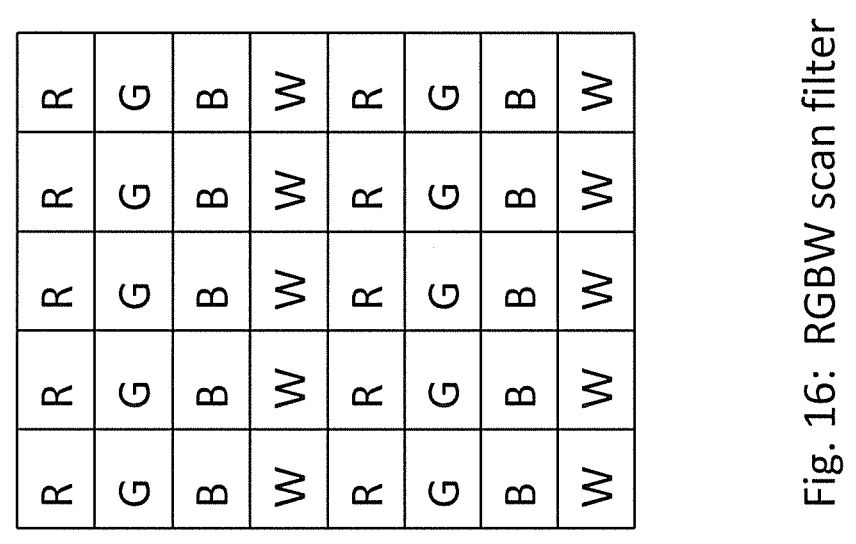

FIG. 16 shows an RGBW Colour Scan Filter Array designed for scanning moving specimens which includes transparent (White) filter elements.

Figure 17:
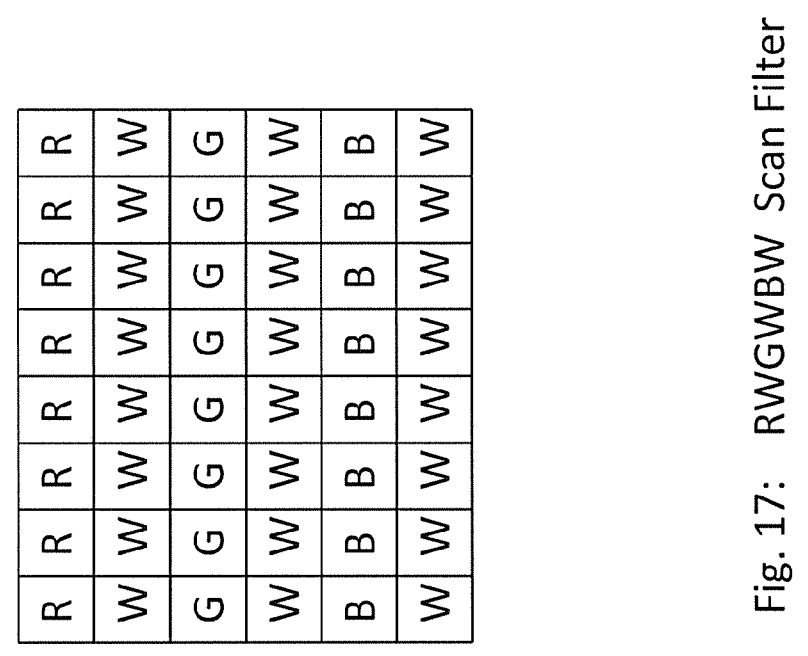

FIG. 17 shows an RWGWBW Colour Scan Filter Array designed for scanning moving specimens which includes a row of transparent (white) filter elements between rows of coloured filter elements.

DESCRIPTION OF THE INVENTION

Figure 1:
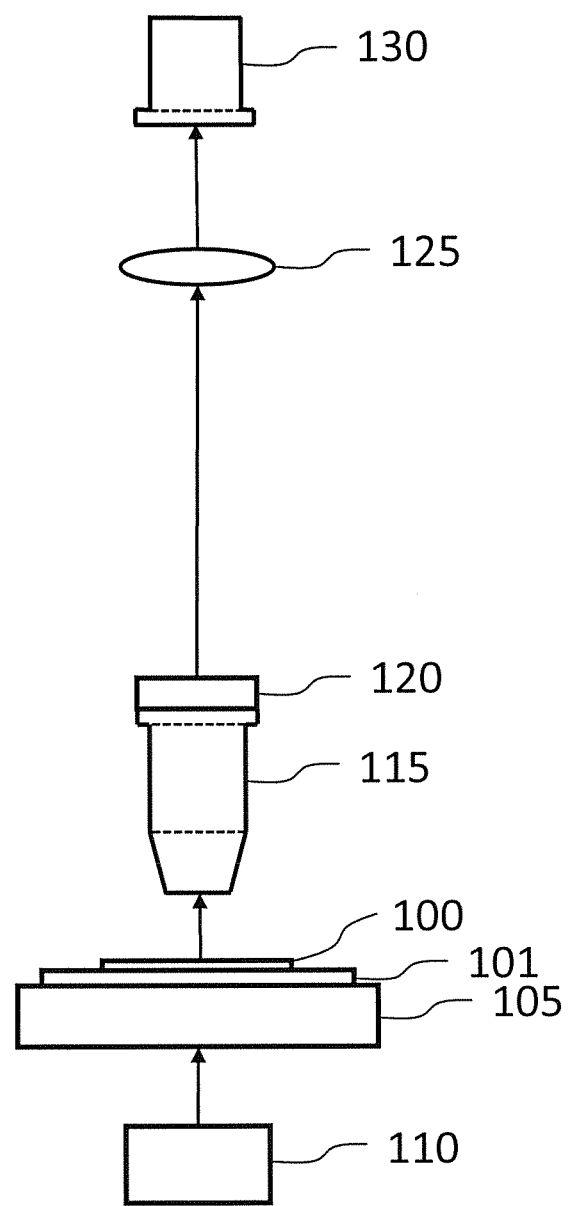
FIG. 1 is a schematic view of a prior-art brightfield microscope slide scanner using a linear or TDI detector array.
Figure 2:
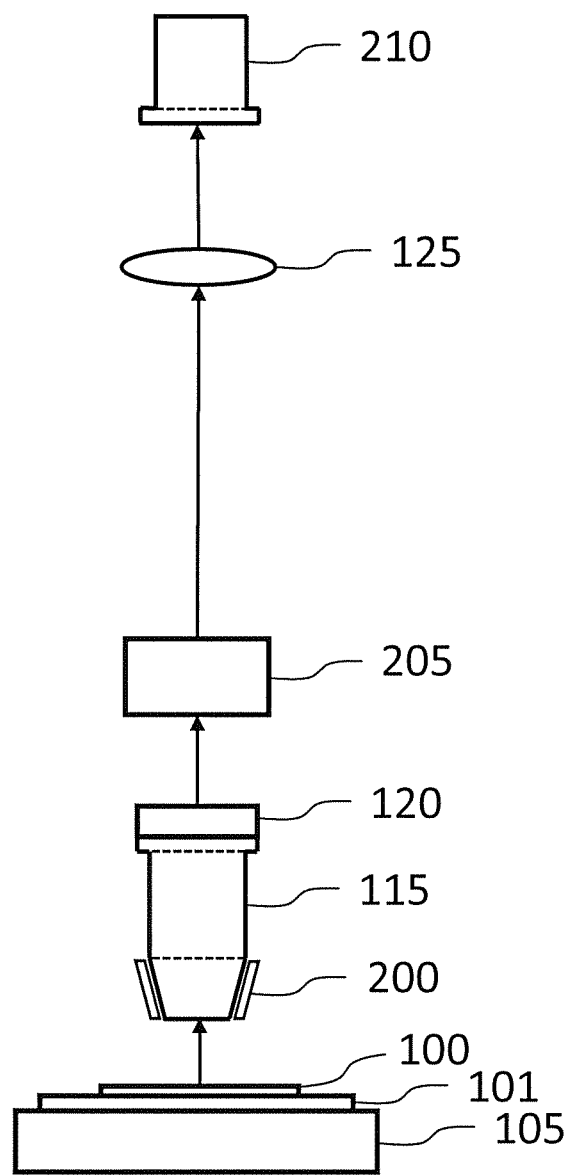
FIG. 2 is a schematic view of a prior-art fluorescence microscope slide scanner using a linear or TDI detector array.
Figure 3:
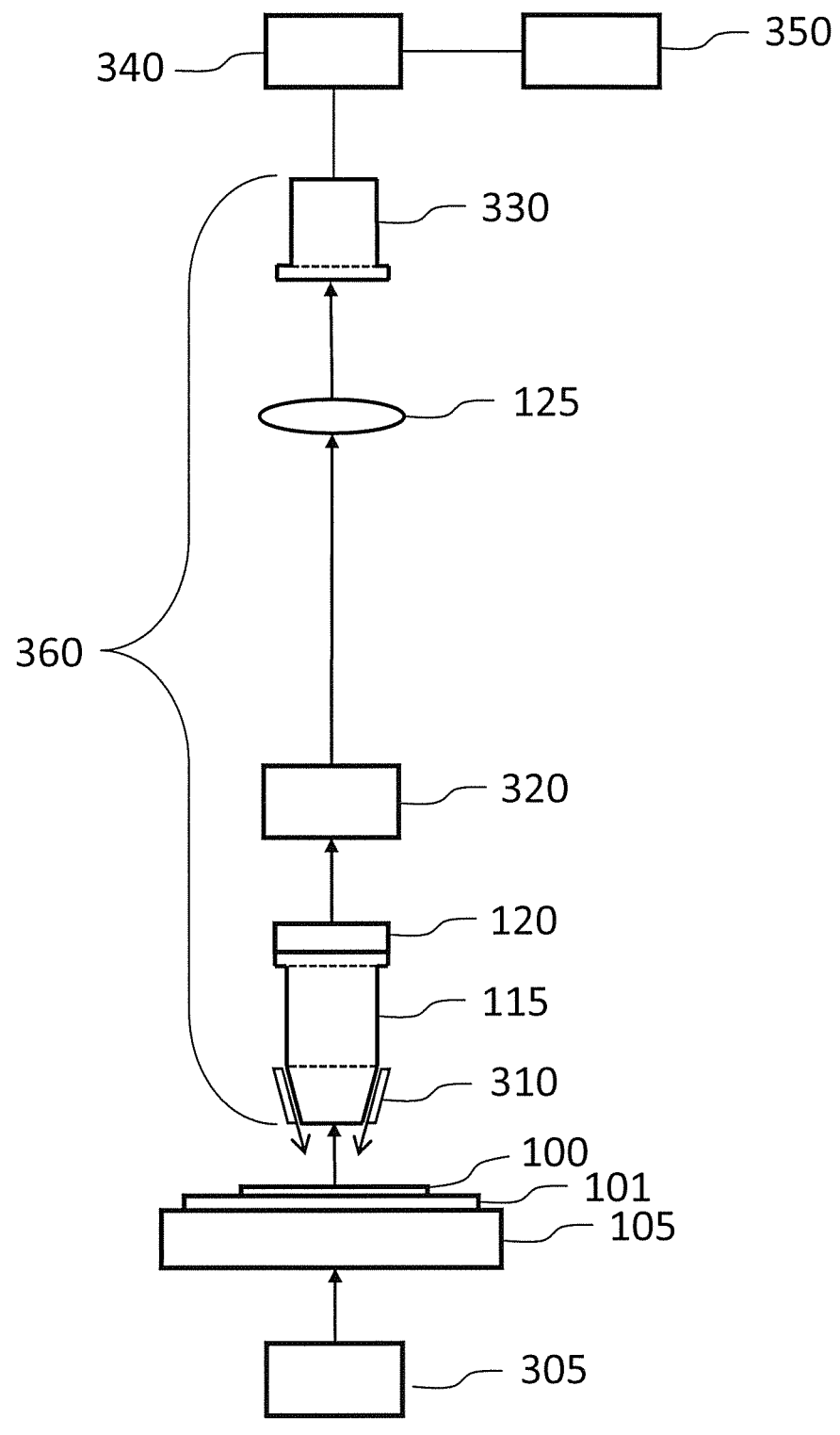
FIG. 3 is a schematic view of a microscope slide scanner for fluorescence and brightfield imaging using an area detector array.

FIG. 3 shows a microscope for fluorescence and brightfield imaging that is a first embodiment of this invention. A tissue specimen 100 (or other specimen to be imaged) mounted on microscope slide 101 on a scanning stage 105. When used for fluorescence imaging, the tissue specimen is illuminated from above by illumination source 310, mounted above the specimen (epifluorescence) so that the intense illumination light that passes through the specimen is not mixed with the weaker fluorescence emission from the specimen, as it would be if the fluorescence illumination source were below the specimen. Several different optical combinations can be used for epifluorescence illumination—light from a source mounted on the microscope objective, as shown; illumination light that is injected into the microscope tube between the microscope objective and the tube lens, imaged onto the back aperture of the objective, using a dichroic beamsplitter to reflect it down through the microscope objective and onto the specimen; and several others. A narrow wavelength band for the illumination light is chosen to match the absorption peak of the fluorophore in use. This narrow-band illumination may come from a filtered white-light source, an LED or laser-based source (including a laser sent through a diffuser plate in rapid motion to eliminate speckle), or other source. Fluorescence emitted by the specimen is collected by infinity-corrected microscope objective 115 (or other high-numerical-aperture objective lens) which is focused on the specimen by piezo positioner 120 (or other focusing mechanism). Emission filter 320 is chosen to reject light at the illumination wavelength and to pass the emission band of the fluorophore in use. The microscope objective 115 and tube lens 125 form a real image of the specimen on two-dimensional detector array 330. An image of the specimen is collected by moving the microscope slide at constant speed using motorized stage 105 in a direction perpendicular to the long dimension of detector array 330, combining a sequence of equally-spaced overlapping two-dimensional images from the array (usually spaced one line apart) to construct a time-integrated image of one strip of the specimen. Data from detector array 330 is read out by frame grabber 340 and passed to computer 350 where strips are then assembled to form a complete image of the specimen.

When used for brightfield imaging, transmitted-light illumination source 305 is used instead of illumination source 310 (which illuminates the specimen from above) and emission filter 320 is removed from the optical train.

Figure 4:
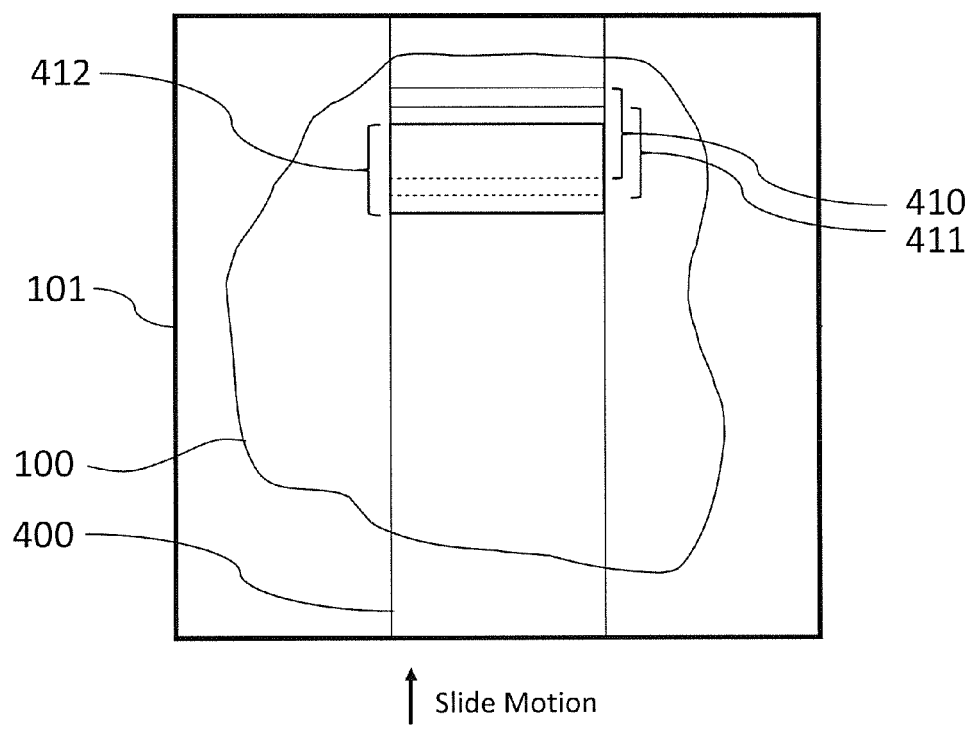
FIG. 4 shows the relative motion of the field-of-view of an area detector array with the motion of a large specimen on a microscope slide which is moving at constant speed on a motor-driven stage.

FIG. 4 shows a specimen 100 mounted on a microscope slide 101. Note that in this diagram the microscope slide is square, but it can have any convenient size and shape, including standard 1×3 inch microscope slides up to very large slides (we have imaged specimens on slides 6×8 inches in size) and for the purposes of this document, the term "microscope slide" includes slides made from glass or other medium (usually but not always transparent) and any other specimen carrier including but not limited to microwell plates and tissue blocks. Specimens may be covered with a cover slip.

Figure 5:
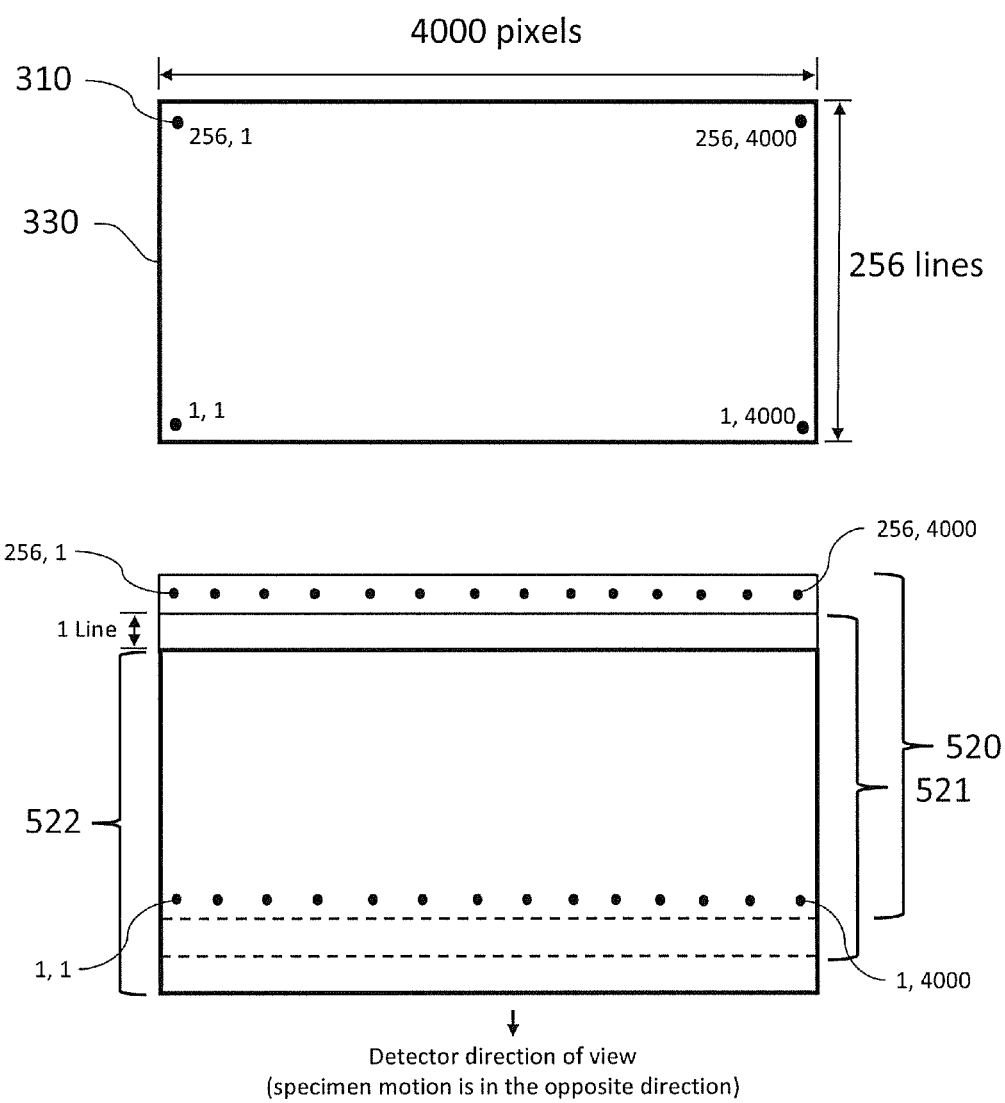
FIG. 5 shows a 256×4000 pixel detector array (top) and the motion of the field-of-view of the array as the stage moves the specimen during scan.

In this diagram, the specimen is larger than the field-of-view 412 of the microscope detector array. In this example, three image strips are required to image the entire specimen 100, but for a larger specimen many more strips may be required. In order to scan specimen strip 400, microscope stage 105 of FIG. 3 moves the microscope slide 101 at constant speed in the direction shown in FIG. 4 (or the microscope optical train 350 is moved at constant speed in the opposite direction). An electronic or mechanical shutter opens for a short time to expose the sensors that make up the two-dimensional detector array 330, which is also shown in detail as detector array 500 in FIG. 5. The exposure time is short enough so that during exposure the constant relative motion of the detector and microscope slide moves field-of-view 410 only part of the way to the adjacent field-of-view 411, which is one pixel away from 410. During the time the shutter is closed, data in the entire two-dimensional detector array is transferred to frame-buffer RAM in a frame grabber 340 or to other electronic frame capture device, and is then transferred to a computer 350. When the field-of-view moves to position 411, the shutter is opened again and a new image frame is collected, the shutter is then closed and this new image is then transferred via the frame grabber to the computer, where this data is added to the image data already stored, but shifted one pixel in the direction of motion of the field-of-view. This process is repeated until a complete image of that specimen strip is stored, starting with a first image frame (first exposure) just above the top edge of the specimen of FIG. 4 to a final image frame just below the bottom edge of the specimen (in order to ensure that every part of the specimen is exposed 256 times, once for each line of pixels in the detector array). For example, the detector array 330 is comprised of 4000 pixels by 256 lines, as shown in FIG. 5 {which shows a CCD or CMOS (or other technology) two-dimensional sensor array 330 with 256 lines of 4000 pixels each (a 256×4000 pixel array)}. Although this particular array has been chosen as an example, arrays with different numbers of pixels and different aspect ratios can also be used. In particular, this means inexpensive arrays manufactured for consumer products can be used if necessary to reduce cost. Using the array shown in FIG. 5, each pixel in the final strip image stored in computer 350 is the sum of 256 exposures of the same pixel position in the specimen. In this particular example, if the frame grabber produces 8-bit images, the resulting stored image has a dynamic range of 16 bits (each pixel is made up of a sum of 256 exposures where each exposure has a maximum value of 255). The fluorescence image of the strip is stored and adjacent strip images are assembled to produce a final image of the specimen. Adjacent strips may be assembled by butting them together, or by collecting overlapping strip images and using feature-matching software for registration.

As an example, using the 256×4000 pixel 8-bit pixel array described above, if a specimen 1 cm long is scanned at 0.25 micron resolution (approx. 40×), a total of 40,255 frames must be acquired in order to expose every pixel 256 times (1 cm×40,000 lines/cm+255). The strip image will contain 40,000×4,000 pixels. If the 16-bit memory locations for each pixel are set to zero before the scan starts, then the value for each pixel at the end of the scan is given by:

$$P_{m,n} = \sum_{i=m}^{i=m+255} p_{\{i-(m-1)\},n,i}$$

where $P_{m,n}$ is the final value for each pixel in the strip image, m is the line number in the strip image (in this example of a 1 cm strip on the specimen, m varies from 1 to 40,000), and n is the column number in the strip image (in this example varies from 1 to 4,000). On the right-hand side of the equation, $p_{\{i-(m-1)\},n,i}$ represents the pixel value for pixels in each detector image frame, where $\{i-(m-1)\}$ represents the row number of the pixel and n represents the column number of the pixel in frame number i. Each pixel P in the final image is the sum of 256 detector image pixels from 256 sequential frames, where the column number varies from 1 to 4,000 (the same number as in the detector image frames) and the row number varies from 1 to 40,000. The running index in the sum is i, and i also equals the frame number (in this example varies from 1 to 40,255).

If the resulting image from the example above is to be viewed in a display with the same dynamic range as the image from each detector frame (8 bits in the example above), the value stored in each pixel position above can be multiplied by 1/N, where N is the number of frames exposed and this value stored in each pixel position in the final image (N=256 in the example above). To ensure the best possible dynamic range in the final image, data contraction as described in WO2009/137935 can be used when converting from an image stored in 16-bit memory locations in order to use the entire dynamic range in the final 8-bit image.

If the scanning stage is set to move at a constant speed of 100 microns/second (1/10 mm/second), and assuming the same 0.25 micron object pixel resolution and 4000×256 pixel detector array as used in the example above, lines of data are collected at 400 lines/second (this is similar to a scan rate of 400 lines/second in a scanning laser microscope or macroscope). If an exposure time of 1/1000 second is used, the moving specimen stage will move less than half the distance between adjacent pixels during the time the shutter is open, and since 256 lines of data from the detector array are summed into each line of data in the final image, the total exposure time for each pixel in the final image is 256/1000 seconds, or approximately 250 milliseconds. By comparison, if a linear detector array is used at the same scan speed, the exposure time is only 1 millisecond, which is too short for weak fluorophores. Note that the operation of the shutter should be closely synchronized with stage motion, just as it must be if TDI detectors were used instead of the two-dimensional detector arrays described in this document. (Note: the specimen image may have enough features to allow sequential image frames to be registered using feature-matching software, which reduces the requirement for synchronization between sequential image frames and therefore would allow a less-expensive moving stage to be used.)

In the example above, the exposure time for each image was 1 msec., leaving approximately 1 msec. to read out the data in the array before the scanning stage has moved a distance equal to the distance between pixels on the specimen. If this read-out time is too short to read out the array, the next exposure can be synchronized to start when the stage has moved a distance equal to an integral number of pixels instead of the distance between adjacent pixels, thus increasing the read-out time while keeping the scan speed unchanged. The number of images added together to form the final image will be reduced by a factor equal to 1/s, where s is the number of pixels the stage moves between exposures. (s=1 when the next exposure is at the next pixel position, s=2 if the next exposure is two pixels distance away, etc.) This technique can also be used to increase the scan speed, while keeping the exposure time constant. If s=16, for example, then only 16 images are added together (or averaged), but the scan speed can be increased dramatically. If the exposure time is kept constant, then the measured pixels will be elongated in the direction of scan, but this may be acceptable if the image collected is a high-speed preview scan, and the dynamic range of data in this preview image can be used to calculate proper exposure for a final, slower scan before that scan starts.

Figure 6:
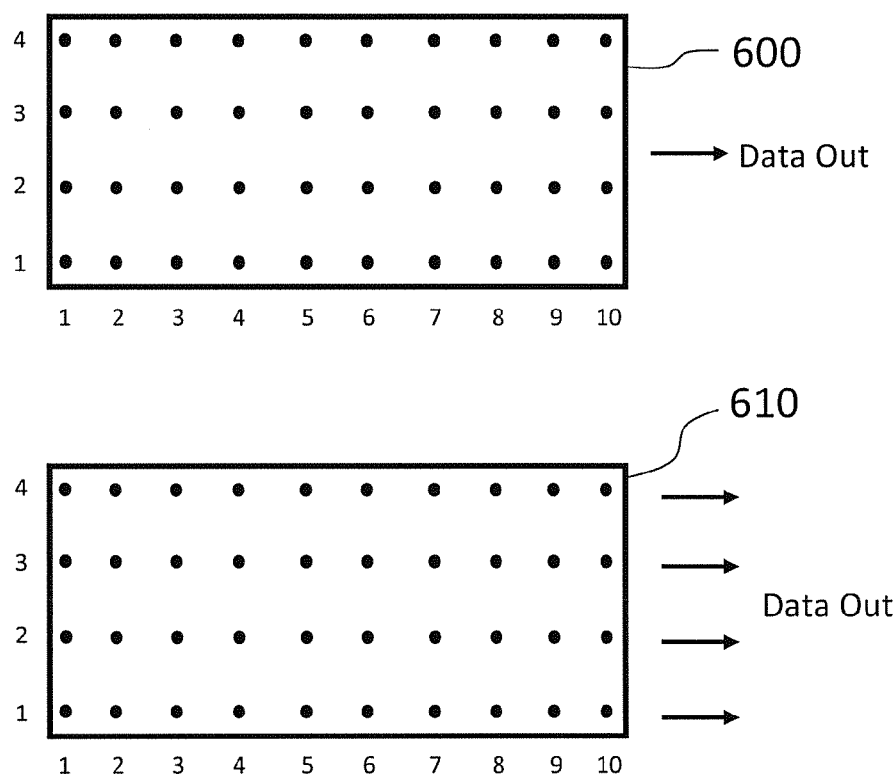
FIG. 6 shows two different output arrangements for a detector array.

FIG. 6 (top) shows a rectangular detector array 600 of 40 pixels (10 pixels by 4 lines). In an ordinary array, the entire frame is read out through the same output port, which can be time consuming (especially for a large array like the 1,024,000 pixel array described in the example above (4000 pixels by 256 lines). FIG. 6 (bottom) shows a second rectangular detector array 610 that also has 40 pixels (10 pixels by 4 lines), but in this array each line is read out through its own output port. Read-out time can be reduced substantially if the lines of data are read out simultaneously into a frame buffer, where they can be stored for further processing. In theory, this could reduce the read-out time of the 1,024,000 pixel array used as example previously by a factor of 1/256. Additionally, since in this application lines of data from the detector array are added in a moving sequence to lines of data stored in a strip image, lines can be shifted and added to the appropriate memory locations in the strip image as parallel processes, thus reducing the computational load as well.

Using this same example of a 4000 pixel by 256 line array, consider a scanner where the required magnification is similar to that from an optical microscope with a 40× objective. The digital image produced by this scanner will have pixels approximately 0.25 microns in size, and 4000 pixels represent the width of a 1 mm wide strip on the specimen. The microscope objective needs a resolving power of 0.5 microns or smaller (numerical aperture of 0.6 or larger), and the Nyquist theorem requires at least two pixels per resolving power for digital imaging {see "Choosing Objective Lenses: The Importance of Numerical Aperture and Magnification in Digital Optical Microscopy", David W. Piston, Biol. Bull. 195, 1-4 (1998) for a good explanation of the requirements for diffraction-limited digital microscopy}. To image 0.25 micron pixels on the specimen onto a detector array with sensors spaced 10 microns apart, the system magnification (objective lens plus tube lens) must be 40×. A microscope objective with a numerical aperture of 0.75 and a focal length of 10 mm is available (this is labeled a 20× objective, but that label assumes a particular tube lens with focal length 200 mm). Since $$\text{Magnification} = f_{tube\ lens}/f_{microscope\ objective},$$

$$f_{tube\ lens} = 40 \times 10 = 400\ mm.$$

The tube lens must be able to form an image at least 4 cm wide for the detector array described above. The combination of an infinity-corrected microscope objective (or other infinity-corrected objective lens) and a tube lens is used because it is possible to insert filters, filter cubes, and beamsplitters into the optical path between the objective and the tube lens without affecting instrument focus and optical performance.

FIG. 7 shows a microscope for fluorescence or brightfield imaging that is a second embodiment of this invention. When used for fluorescence imaging, a tissue specimen 700 (or other specimen to be imaged) which has been stained with three different fluorescent dyes is mounted on microscope slide 101 on a scanning stage 105. The tissue specimen is illuminated from above by illumination source 705, mounted above the specimen (epifluorescence) so that the intense illumination light that passes through the specimen is not mixed with the weaker fluorescence emission from the specimen, as it would be if the illumination source were below the specimen. Several different optical combinations can be used for epifluorescence illumination—light from a source mounted on the microscope objective, as shown; converging illumination light that is injected into the microscope tube between the microscope objective and the tube lens that focuses on the back aperture of the objective, using a dichroic beamsplitter to reflect it down through the microscope objective and onto the specimen; and several others. Narrow wavelength bands are chosen for the illumination light to match the absorption peaks of the fluorophores in use. This narrow-band illumination may come from a filtered white-light source, an LED or laser-based source (including an amplitude or frequency-modulated laser or LED source), or other source. Fluorescence emitted by the specimen is collected by infinity-corrected microscope objective 115 (or other high-numerical-aperture objective lens) which is focused on the specimen by piezo positioner 120 (or other focusing mechanism). Dichroic mirror 730 is chosen to reflect light in the emission band of the first fluorophore towards tube lens 710 placed in front of two-dimensional detector array 720. Microscope objective 115 and tube lens 710 form a real image of the specimen on two-dimensional detector array 720. Data from the two-dimensional detector array is collected by frame grabber 770 or other electronic frame capture device and passed to computer 350.

Light from the specimen 700 that was not reflected by dichroic mirror 730 continues up the microscope to reach dichroic mirror 740, which is chosen to reflect light in the emission band of the second fluorophore towards tube lens 750 placed in front of two-dimensional detector array 760. The microscope objective 115 and tube lens 750 form a real image of the specimen on two-dimensional detector array 760. Data from this two-dimensional detector array is read out by frame grabber 780 or other electronic frame capture device and passed to computer 350.

Light from the specimen 700 that was not reflected by dichroic mirrors 730 and 740 contains light in the emission band wavelengths for fluorophore three, and continues up the microscope to reach tube lens 125, in front of two-dimensional detector array 330. The microscope objective 115 and tube lens 125 form a real image of the specimen on two-dimensional detector array 330. Data from this two-dimensional detector array is read out by frame grabber 340 or other electronic frame capture device and passed to computer 350.

An image of the specimen is collected by moving the microscope slide at constant speed using motorized stage 105 in a direction perpendicular to the long dimension of the three detector arrays 720, 760 and 330 (which are all oriented with the long dimension of the arrays perpendicular to the motion of the real images projected on them by the microscope objective 115 and tube lenses 710, 750 and 125 respectively). A sequence of equally-spaced overlapping two-dimensional images from the each of the three arrays is passed to computer 350 by frame grabbers 770, 780 and 340 where three time-integrated images of one strip of the specimen are constructed, one for each fluorophore. These three images can be viewed separately (fluorescence images are essentially greyscale images) or combined using false colours into a colour image for viewing. In many cases the false colours are chosen to make the final image look like the image that would be seen through a fluorescence microscope.

FIG. 7 shows a scanner with three detection arms, one for each of three fluorophores (a scanner can also be envisioned for other numbers of fluorophores). In particular, if quantum dots (nanocrystals) are used as a contrast agent in fluorescence, several detection arms can be used. This is possible because quantum dots can be manufactured with very narrow emission bands, and they are inherently brighter and more stable than fluorophores. In addition, all quantum dots in a specimen can be excited with the same excitation wavelength, so a single wavelength source can be used which is not in the emission bands of any of the dots in the specimen, making it easier to separate the emission signals.

When used for brightfield imaging, white light source 110 is used to illuminate the specimen from below (instead of using light source 310), and the dichroic mirrors 730 and 740 are chosen to separate the colours detected by area detectors 770, 780 and 340 into red, green and blue. Images from each of the three detection arms are combined to produce a colour brightfield image. If area detector 340 is replaced by an RGB detector, dichroic mirrors 730 and 740 can be removed from the optical train and the single colour detector will produce a colour brightfield image.

Instead of using three detection arms, as shown in FIG. 7, it is also possible to use a trichroic prism to separate light emitted from three fluorophores to be focused on three ccd detectors. Such an assembly can also be used for RGB brightfield imaging.

FIG. 8 shows a third embodiment of this invention, a scanner in which a tunable filter 810 is used to provide a multi-spectral fluorescence slide scanner and method for imaging large specimens mounted on microscope slides. The tunable filter can be set to transmit a band of emission wavelengths from one fluorophore (or other fluorescent source) and a strip image recorded for that source, followed by setting a second wavelength band for a second fluorophore to record a strip image for that source, and so on until a strip image has been recorded for each fluorescence source in the specimen. The strip images can either be viewed separately or combined into a single image (usually false coloured) and the strips can then be assembled into a single image of the entire specimen. This instrument can also be used for brightfield imaging by replacing epifluorescence source 705 with white light transmission source 110, and using the tunable filter 810 to pass red, green and blue wavelengths to record red, green and blue strip images in sequence which can be combined into a single RGB brightfield image.

FIG. 9 shows a single two-dimensional CCD (or other technology) array 900 in which the top third 910 of the array is covered with a red transmission filter, the middle third 920 is covered with a green transmission filter, and the bottom third 930 is covered with a blue transmission filter. Such an array can be used to simultaneously image three colours, for example red, green and blue for brightfield imaging, or three different fluorophores in multi-spectral fluorescence (where the transmission filters are chosen with bandwidths that match the fluorescence emission peaks).

FIG. 10 shows a fourth embodiment of this invention, a scanner in which a detector array 900 (covered with red, green and blue transmission filters as discussed above) simultaneously records three strip images (red, green and blue) when white light transmission source 110 is used to illuminate the specimen from below. Image data from the top third 910 of array 900 is used to record the red image, data from the middle third 920 of array 900 is used to record the green image, and that from the bottom third 930 of array 900 is used to record the blue image. Each of these images is recorded in separate strip images that can be combined into an RGB image after the scan for that strip is completed. Note that FIG. 9 shows a 4000 pixel×256 line array—this is for example only—arrays with different pixel number width and number of lines can also be used.

For fluorescence imaging, the epifluorescence light source 310 (or other epifluorescence source) is used instead of white light source 110, and transmission filters are chosen to cover fractions of the array 900, one matching the peak of the emission band of each fluorophore in the specimen. In particular, if fluorescent nanoparticles are used as the fluorescence source, a filter is chosen with transmission bandwidth to match the emission peak of each of the nanoparticles, and fluorescence from several nanoparticles can be imaged simultaneously.

FIG. 11 is a schematic representation of a scanning fluorescence microscope that is a fifth embodiment of this invention. Light from white light source 1110 passes through tunable filter 1120, is partially reflected by beamsplitter 1130, passes through microscope objective 115, and illuminates an area of the surface of specimen 100, which is mounted on microscope slide 101 on moving microscope stage 105. Motion of the microscope stage is in a direction perpendicular to rows in the detector array {data is read out from rows in the detector array, usually the long dimension of the array (for example see Hamamatsu's ORCA-flash 4.0 camera, or PCO's pco.edge camera, both of which use Scientific CMOS (sCMOS) detector arrays)}. Fluorescence emitted from the specimen is collected by microscope objective 115, is partially transmitted by beamsplitter 1130, and then passes through tunable filter 810 and is focused by tube lens 125 onto detector array 330, which is not covered by a colour filter array. Data from the detector array 330 is read out by frame grabber 340 and passed to computer 350 where an image strip is assembled for each fluorophore.

As an example, suppose there are two fluorophores in the specimen. Tunable filter 1120 is adjusted to transmit the appropriate excitation wavelength range for the first fluorophore, and tunable filter 810 is adjusted to transmit the emission wavelength band of the first fluorophore. Detector array 330 is read by frame grabber 340 which passes the data for the first image frame to computer 350, which stores this image frame at the beginning of a first strip image. The microscope stage is moved a distance equal to the distance required to move the image projected on the detector array by tube lens 125 a distance equal to the distance between rows in the array. Tunable filter 1120 is then adjusted to transmit the appropriate excitation wavelength range for the second fluorophore, and tunable filter 810 is adjusted to transmit the emission wavelength band of the second fluorophore. The first image frame for fluorophore 2 is stored in a second strip image. Next, the microscope stage is moved a distance equal to the distance required to move the image the distance between pixels in the detector array, and a second image of the first fluorophore is collected, moved in the scan direction a distance equal to the distance between pixels, and added to the first image already stored in the strip image for the first fluorophore. Imaging continues from one fluorophore to the other until the entire strip of specimen has been imaged and a strip image has been collected for each fluorophore. In operation, the scanning stage usually moves at a constant speed, and the tunable filters are synchronized with the motion to produce one exposure every time the stage has moved a distance that is equivalent to the distance between image pixels. In this case (when two fluorophores are present), each image frame from the detector is moved by one pixel in the scan direction from the image before it, so when each image is added to one of the fluorophore strip images, it must be displaced by 2 pixels. When three fluorophores are present, three images are collected during the time the stage moves a distance that will cause the moving image to move a distance equal to that between three rows of pixels in the detector array, and the tunable filters are synchronized to provide the appropriate excitation and emission wavelengths during the specimen motion. Alternatively, when two fluorophores are used for example, the specimen stage can be moved a distance equivalent to half the distance between image pixels between exposures and the tunable filters can be synchronized to change excitation and emission wavelengths each time the stage has moved a distance equivalent to half the distance between image pixels. This has the advantage that the number of exposures of the same area of the specimen is doubled, but scan speed is reduced and the two image strips are now out of registration by ½ pixel in the scan direction.

Several other optical arrangements in addition to that shown in FIG. 11 are possible. For example, tunable filters 810 and 1120 can be replaced by rotating optical filters or filter wheels that are synchronized to each other and to stage motion to pass the appropriate excitation and emission wavelengths. FIG. 12 shows one example of a pair of rotating optical filters designed for use for simultaneous imaging of three fluorophores, with first rotating optical filter 1210 (which replaces tunable filter 1120 in FIG. 11) designed to pass three excitation wavelength bands X1, X2 and X3, chosen to excite the three fluorophores known to be present in specimen 100. Second rotating optical filter 1220 replaces tunable filter 810, and is designed to pass the three emission bands E1, E2 and E3 of the three fluorophores present in the specimen. The rotation of these two optical filters is synchronized so that excitation filter X1 and emission filter E1 are both positioned in the optical path at the same time (as are X2 and E2, and X3 and E3), and their rotation is further synchronized with the motion of the scanning stage so that the stage moves a distance such that the image of the specimen projected on the detector array moves a distance equal to the distance between rows in the array during the time the filters rotate 120 degrees.

As a second example, a tunable light source can be used in place of the combination of white Light Source 1110 and tunable filter 1120 to provide an excitation wavelength band that is appropriate for the fluorophore in use.

As a third example, a tunable light source placed in the epifluorescence position shown by light source 310 in FIG. 3 and synchronized with stage scan and the tunable emission filter 810 can replace white light source 1110 and tunable filter 1120.

As a fourth example, if a white light illumination source is placed below the specimen (like light source 305 in FIG. 3), then tunable filter 810 can be adjusted sequentially to pass red, green and blue, and R, G and B strip images can be acquired simultaneously and assembled after scanning into a single RGB image. (Note: instead of collecting three strip images during scanning, and assembling three strip images to produce a single RGB image after scanning, data can be added to or averaged with data already present in the R, G and B components of a single RGB strip image if that is more convenient for data flow.) The addition of a white illumination source below the specimen has resulted in a scanner that performs both brightfield and fluorescence imaging. If beamsplitter 1130, tunable filter 1120 and white light source 1110 are removed, this becomes a brightfield-only scanner. The further addition of a tunable light source in the same position as light source 310 in FIG. 3 (an epifluorescence position) results in a brightfield and fluorescence scanner.

When a white light source is placed below the specimen for transmission brightfield imaging, a rotating filter like RGB filter 1220 can be used either to filter the incoming light from the source (where the filter is placed between the white light source and the specimen) or to filter light collected by the objective lens (where the filter is placed between the objective lens and the tube lens). When filter rotation is synchronized with stage scan, either of these arrangements can be used to produce a colour brightfield scanner. Other colour combinations are possible, including but not limited to RGBW, CYGM and RGBE. When used in this manner, no colour filter array is required on the detector array, and the images do not require demosaicing.

FIG. 13 is a schematic representation of a scanning brightfield microscope that is a sixth embodiment of this invention. In this embodiment, area detector array 1300 contains a mosaic Colour Filter Array (a Bayer filter, which is commonly used in single-chip colour cameras). Images acquired using a Bayer filter (or other common mosaic filters) are normally demosaiced using a computer algorithm before viewing, but this will not be necessary when Moving Specimen Image Averaging is used. A small 4×4 pixel area array 1410 using a Bayer filter is shown on the left side of FIG. 14. This small array example is used to explain how an area array using a Bayer filter can be used for Moving Specimen Image Averaging, however in practice much larger arrays are used (for example, 2560×256). The first exposure in a scan using the small array 1410 is shown at the top of FIG. 14*a*. Three strip images are set up in RAM in computer 350, one strip each for red, green and blue, and data values in each pixel position are initially set to zero. Data from the first exposure is transferred to each of the strips, resulting in red strip image 1421, green strip image 1431, and blue strip image 1441, as shown at the top of FIG. 14*a*. When the stage has moves a distance such that the image on the detector has moved a distance equal to the distance between rows of detector pixels, a second exposure is acquired, and data from this second exposure is transferred to the colour strip images, resulting in strip images 1422, 1432 and 1442. The results after adding data from exposure #3 to the data already stored in the three image strips is shown in FIG. 14*b* (top), and results after exposures 4 and 5 are shown in FIG. 14*b* (bottom) and FIG. 14*c*. At the end of the first five exposures, data in rows 4 and 5 of each strip image are complete (for a detector with only four rows, no additional data will be added to rows 4 and 5 of the strip images as the scan continues). Note that after four exposures, row 4 in the final image strips contains two exposures of pixel R1 and R3, two exposures of all four Green pixels (G1, G2, G3 and G4) and two exposures of pixels B2 and B4. After the fifth exposure (row 5 from the top of the three strip images), it is obvious that the same pixel positions have been exposed in the fifth row, with the same exposure. After the scan has been completed (assume several hundred rows have been exposed), the first 3 rows of data should be discarded (because they are not fully exposed), and the last 3 should also be discarded. Also note that the final red and blue images have full resolution in the vertical direction, but resolution in the horizontal direction is only half as good. The green image has full resolution in both directions. The green image requires no interpolation before assembling the three strips to produce a final RGB image, but both the red and blue images will require some interpolation to fill in the blanks. The simplest interpolation (which may be good enough in many cases) is simply to average the red or green pixels on either side of an empty pixel position. More complex interpolation could include an algorithm that includes changes in local brightness using the green pixels, or nearest neighbor interactions between adjacent pixels. Since a single chip colour camera was used to take all of the separate images, the colour image resulting from each exposure can be demosaiced and then added to the demosaiced images resulting from subsequent exposures using MSIA, but this is a calculation-intensive process that will not be necessary in most applications, and slows down image acquisition.

A more realistic situation is one where the detector array is much larger than the 4×4 pixel array shown in FIG. 14. Assume that the same RGGB Bayer filter is used. If the array has 256 rows and 2560 columns of pixels, then each image strip is 2560 pixels wide. The first row to be fully exposed (after exposure #256) will be row 256 in each strip image (the first 255 rows of image data should be discarded), each green pixel will have been exposed 128 times, and the same rows of red and blue pixels as shown in FIG. 14*c* will be exposed 128 times, or not at all. The final 255 rows in the image strip should be discarded. Since a 1 cm scan contains 40,000 rows of data (assuming ¼ micron pixels), discarding the first 255 and last 255 rows will not increase the scan time very much.

When a colour camera with a Bayer filter (or other common Colour Filter Array) is used, after scanning is complete it is possible to return to areas of interest that have been identified in the scanned image to view those areas in either a single-field-of-view or tiling-microscope mode, and to collect 4D colour image data from those areas (X, Y, Z, time). This instrument and method (the sixth embodiment) uses a mosaic Colour Filter Array, and is used for brightfield scanning of large specimens using MSIA (where no demosaicing of the image is required), as well as real-time and 3D imaging of small areas of interest (in which the images are mosaiced in the normal way for instruments using mosaic Colour Filter Arrays).

The Bayer filter (and other common Colour Filter Arrays) were designed for cameras in which an entire colour image is captured in a single exposure. As discussed above, such filters can also be used for microscope slide scanners using Moving Specimen Image Averaging, but when the Bayer filter is used in that application the resolution of red and blue pixels in the horizontal direction is only half that in the vertical direction. The green pixels have full resolution in both directions. Interpolation is necessary to fill in the missing red and blue pixels in the horizontal direction, but this interpolation is much simpler than the demosaicing usually used with Bayer filter cameras. Many cameras are commercially available with Bayer filters, which is an advantage.

A two-dimensional sensor array in which the top third of the array was covered with a red transmission filter, the middle third was covered with a green transmission filter, and the bottom third was covered with a blue transmission filter, was shown in FIG. 9. This colour filter array is not useful for capturing an entire colour image in a single exposure, but is useful for scanning using Moving Specimen Image Averaging, and results in a final strip image in which all three colour components of the image have maximum resolution in both directions. We define this and other Colour Filter Arrays that are used only for scanning as "Scanning Colour Filter Arrays" (SCFA). Several additional embodiments of Scanning Colour Filter Arrays are described below. FIG. 9 shows a first embodiment of a Scanning Colour Filter Array.

FIG. 15 shows a second embodiment of a Scanning Colour Filter Array. This SCFA is shown on a 5×6 pixel sensor array (top left), with the data flow from the first exposure to the image store for red, green and blue monochrome images (or to the R, G and B components of a single RGB image) on the right. The second exposure is shown at the bottom of FIG. 15, after the moving stage has moved a distance such that the image on the detector has moved a distance equal to the distance between rows of detector pixels. Data from the rows of Red, Green and Blue pixels is transferred to the image store and fills in the next rows of R, G and B pixel image data. After the third exposure, the rows of R, G and B pixels in the R, G and B images will be completely filled in (not shown). Note that all three images have full resolution in both the horizontal and vertical directions, and no interpolation is required. As the scan proceeds, data is transferred from the detector array to the image store after each exposure. For a Scanning Colour Filter Array in which there are two RGB sequences in the vertical direction (as shown in this example), each pixel in the final R, G and B images will be exposed twice and averaged together using Moving Specimen Image Averaging. In a more practical example, for example a 2560×258 pixel array, 86 rows are covered with a Red filter, 86 are covered with a Blue filter, and 86 are covered with a Green filter, in the same RGB sequence as shown in FIG. 15. Red, Blue and Green pixels are averaged 86 times. When low light levels are used, random noise can seriously degrade the resolution of a microscopy image, and this is especially true in fluorescence, where light levels are often very low. Image averaging improves noisy images dramatically, with a signal/noise ratio improvement proportional to the square root of the number of exposures. In this case, where each image pixel is exposed 86 times and averaged using MSIA, signal/noise ratio of a noisy image is increased by a factor of 9.3, which improves the image considerably.

FIG. 16 shows a four-line sequence RGBW Scanning Colour Filter Array that is a third embodiment of a Scanning Colour Filter Array. The addition of a row of white (panchromatic) pixels with three rows of colour pixels adds several new possibilities for scanned images using MSIA. For example, the clear (white) pixels are the brightest pixels in the array, and result in a panchromatic image strip that is the brightest of the four images and can also be used to detect infrared. This image will have the best contrast of the four images, and will be useful for image processing later since it is perfectly registered with the three single-colour images. When the four-line sequence RGBW scanning colour filter array shown in FIG. 16 is used on a 2560×256 sensor array, each of the four images will be composed of pixels that have been exposed 64 times, and after MSIA the signal/noise ratio in each image will have been increased by a factor of 8.

Because of its brightness and high contrast, the white image will be useful for autofocusing, and can also be used for fluorescence imaging (the R, G and B images can be ignored or discarded when not required) with the addition of a fluorescence light source and emission filter. For single-fluorophore imaging, the light source and emission filter do not have to be synchronized with the scanning stage, and can be implemented using a white light epifluorescence source and filter cube. A standard fluorescence microscope, with the addition of a scanning stage and a brightfield/fluorescence MSIA camera (a single-chip camera using an RGBW or RWGWBW Scanning Colour Filter Array), can be used for both RGB and fluorescence scanning. A second fluorophore can be imaged simply by changing the filter cube in the microscope and scanning again.

A third example of a Scanning Colour Filter Array is shown in FIG. 17, an RWGWBW Scanning Filter Colour Array. In this array a row of clear (white) pixels is placed after each row of colour pixels. This filter array results in four images, as the RGBW array did, however in this case the exposure of the panchromatic image will be three times that of each of the colour images. This is particularly important for fluorescence imaging, where signal strength is low and there is considerable background noise. In this case, using a 2560×256 pixel array, each of the single-colour images will be exposed 42 times, and each panchromatic image will be exposed 128 times. This results in increased signal/noise ratio in the fluorescence image (where it is required) compared to each of the R, G and B images.

I claim:

1. A scanning microscope for obtaining a final contiguous colour image of at least a portion of a specimen, the microscope comprising:
   a) an illumination system to illuminate a part of the specimen being scanned;
   b) at least one lens that focuses light from the specimen onto a two dimensional sensor array, the specimen mounted on a support that is movable relative to the two dimensional sensor array;
   c) the two dimensional sensor array having a plurality of rows and columns, and having a colour filter array, the colour filter array that is one selected from the group of:
      (i) a mosaic colour filter; and
      (ii) a scanning colour filter array having a plurality of at least XN rows with each row being one colour, N being the number of adjacent rows of the same colour and being equal to or greater than one, X being the number of different colours and being equal to or greater than three, the XN rows forming a pattern, a sequence of the pattern being repeated as required to cover the entire sensor array, the scanning colour filter array having a plurality of rows of each colour;
   d) the sensor array having a shutter, the shutter synchronized to open, acquire a two dimensional image frame of the specimen and close with the motion of the specimen relative to each line of the sensor array each time that an optical image of the specimen has moved a distance that is equal to the distance between adjacent rows of the sensor array, the sensor array acquiring image frames when the shutter is open and data for the image frames acquired being transferred to a frame capture device when the shutter is closed, the sensor array acquiring multiple image frames of the specimen in one or more image strips, each image frame comprising a plurality of adjacent lines of the sensor array and immediately adjacent image frames each shifted from one another by one line of the sensor array, the sensor array acquiring a two dimensional image frame of the specimen each time that the shutter opens and closes;
   e) each image strip having a width equal to a width respectively of the colour filter array, the colour filter array having a length and width corresponding to the length and width respectively of the sensor array;
   f) a processor programmed:
      (i) to receive data for all image frames acquired, as the opening and closing of the shutter is repeated numerous times the data for newly acquired image frames is averaged with or added to the data already stored each time creating a lengthening strip image of one of the one or more image strips, the data for all image frames acquired and the image strips are created simultaneously for each image strip and the image frames are accessible to the processor as the data is acquired;
      (ii) to assemble all of the image strips acquired; and
      (iii) to average adjacent nearest pixel values of the same colour when required to produce full colour information at each pixel position in the strip image and to create and store a final contiguous colour image of the portion of the specimen scanned, the final image containing full colour information at each image pixel position for each colour of the colour filter array.

2. The scanning microscope as claimed in claim 1 wherein the support moves the specimen relative to the detector array at a constant speed and the colour filter array is a mosaic colour filter having a plurality of rows with each row having detector pixels of two colours, adjacent rows differing from one another by at least one colour, the processor programmed to create one image strip, for each colour, there being a plurality of image strips:
   the processor further programmed to assemble the plurality of image strips to create the final contiguous colour image, the instrument set up to acquire at least one of brightfield or fluorescence colour images.

3. The scanning microscope as claimed in claim 2 wherein the colour filter array is a Bayer filter.

4. The scanning microscope as claimed in claim 1 wherein the colour filter array is a mosaic colour filter array having a plurality of rows with each row having an equal number selected from the group of two colours of green, red, blue, and white detector pixels, adjacent rows having different colours, the processor further programmed to assemble the red, green and blue image strips to create a final contiguous colour image and a grey strip image using the white pixels, the instrument set up to acquire at least one of brightfield or fluorescence colour and grey scale images.

5. The scanning microscope as claimed in claim 1 wherein the colour filter array is a scanning colour filter array and the instrument moves the specimen relative to the detector array at a constant speed.

6. The scanning microscope as claimed in claim 5 wherein N is equal to 1 and X is equal to 3, there being at least six rows of the scanning colour filter array, a sequence of at least three rows having different colours being repeated at least once, the processor programmed to create one image strip for each colour and the microscope having a set up to acquire at least one of brightfield or fluorescence colour images.

7. The scanning microscope as claimed in claim 2 wherein the instrument is a spinning disk confocal microscope that is used for brightfield scanning without demosaicing data from the mosaic colour filter array when the specimen is moving relative to the mosaic colour filter array during the scan, the spinning disk confocal microscope alternatively being used for real-time imaging of small areas of interest in the specimen where the specimen is stationary relative to the mosaic colour filter array when the images are taken, the images taken when the specimen is stationary relative to the mosaic colour filter array are still images and requiring demosaicing in order to be viewed.

8. The scanning microscope as claimed in claim 1 wherein the colour filter array is a scanning colour filter array with at least six rows, and all detector pixels in a row in the scanning colour filter array are of the same colour with adjacent rows having different colours, a sequence of at least three rows having different colours being repeated at least once, when used for MSIA (Moving Specimen Image Averaging) scanning high resolution colour images result with no interpolation being required.

9. A scanning microscope for scanning and obtaining a colour image of at least a portion of a specimen, the microscope comprising:
 a) an illumination system to illuminate a part of the specimen being scanned,
 b) at least one lens that focuses light from the specimen onto a two dimensional sensor array, the specimen being mounted on a support that is movable relative to the two dimensional sensor array,
 c) the two dimensional sensor array having a colour filter array and a shutter, the shutter synchronized to open, acquire a two dimensional image frame of the specimen and close as the specimen is scanned through the colour filter array for a plurality of adjacent lines of the sensor array as the specimen moves continuously line by line relative to the sensor array, each image comprising a plurality of adjacent lines of the sensor array immediately adjacent images each shifted from one another by one line of the sensor array,
 d) a processor programmed to receive data for all image frames acquired for each of the image strips from the sensor array each time that the shutter of the sensor array opens and closes, each time that the shutter closes image data from newly acquired images is averaged with or added to the data already stored creating a lengthening strip image of the one or more image strips, the processor programmed to average adjacent nearest pixel values of the same colour when required to produce full colour information at each pixel position in the strip image and to create and store a final contiguous colour image of the portion of the specimen scanned, the final image containing full colour information at each image pixel position for each colour of the colour filter array.

10. The scanning microscope as claimed in claim 9 wherein the microscope scans the specimen using Moving Specimen Image Averaging and the specimen moves relative to the detector array at a constant speed.

11. The scanning microscope as claimed in claim 10 wherein the microscope acquires brightfield colour images and the colour filter array is a mosaic colour filter array.

12. The scanning microscope as claimed in claim 9 wherein the microscope scans the specimen in fluorescence using Moving Specimen Image Averaging and the colour filter array is a scanning colour filter array;
 (i) having at least six rows with each row being one colour, and adjacent having different colours, a sequence of at least three rows having different colours being repeated at least once:
 (ii) a plurality of at least eight rows, with each row being one colour and adjacent rows having different colours, a sequence of at least four rows having different colours being repeated at least once; or
 (iii) a plurality of at least XN rows with each row being of one colour, N being the number of adjacent rows of the same colour and being equal to or greater than two, X being the number of different colours and being equal to or greater than three, the XN rows forming a pattern, a sequence of the pattern being repeated if there are one or more repetitions of the XN rows.

13. The scanning microscope as claimed in claim 9 wherein the instrument scans the specimen in fluorescence using Moving Specimen Image Averaging.

14. The scanning microscope as claimed in claim 13 wherein the support is a movable stage.

15. The scanning microscope as claimed in claim 5 wherein the final image is viewable without demosaicing or interpolation.

16. The scanning microscope as claimed in claim 14 wherein the microscope is a spinning disk confocal microscope that is used for fluorescence scanning.

17. The scanning microscope as claimed in claim 5 wherein N is equal to 1 and X is equal to 4 in the scanning colour filter array, the colours being red, blue, green and white, the scanning colour filter array having at least eight rows with a colour pattern in a first four rows being repeated at least once, the processor programmed to assemble the image strips to create the final contiguous colour image without interpolation, the instrument being set up to acquire brightfield or fluorescence colour images.

18. The scanning microscope as claimed in claim 17 wherein the at least one white row of pixels is used for auto focusing or for fluorescence imaging.

19. A scanning colour imaging array comprising
 a two dimensional sensor array,
 a colour filter array comprising a plurality of rows where all detector pixels in each row have the same colour, but the colour differs between adjacent rows, the filter array having at least eight rows, at least two rows of which contain white detector pixels, at least two rows of which contain red detector pixels, at least two rows of which contain green detector pixels and at least two rows of which contain blue detector pixels, a pattern of colours repeating every four rows, the colour filter array being optimized for Moving Specimen Imaging Averaging by which an instrument acquiring images of an area of a specimen as the specimen moves line by line relative to the two dimensional sensor array, the two dimensional sensor array having a shutter synchronized to open, acquire a two dimensional image frame of the specimen and close as the specimen is scanned through the scanning colour filter array for a plurality of lines of the sensor array, a processor programmed to receive data for the images from each of the image strips from the sensor array each time that the shutter of the sensor array opens and closes, the processor programmed to add to the data already stored the data for newly acquired images each time that the shutter closes, thereby creating a lengthening strip image of the one or more image strips, the processor further programmed to produce a final contiguous colour image from all of the image strips, the final image containing full colour information at each image pixel position for each colour of the filter array.

20. A method of scanning a specimen using a scanning microscope having a light source and an optical train having at least one lens to focus light from the specimen onto a two dimensional sensor array, the specimen being mounted on a support that is movable relative to the two dimensional sensor array, the method comprising using a mosaic colour filter array with the two dimensional sensor array, the sensor array having a shutter and moving the specimen and specimen support line by line relative to the sensor array while scanning the specimen and synchronizing the shutter to open, acquire a two dimensional image frame of the specimen and close as the specimen is scanned for a plurality of lines of the sensor array, there being one or more image strips, each image frame comprising a plurality of adjacent lines of the sensor array and immediately adjacent image frames each shifted from one another by one line of the sensor array, the sensor array acquiring a two dimensional image each time that the shutter opens and closes, and programming a computer to receive data for the images from each of the image strips from the sensor array each time that a shutter of the sensor array opens and closes, programming the computer to average with or add to the data already stored the data for newly acquired image frames each time that the shutter closes, thereby creating a lengthening strip image of the one or more image strips, programming the processor to average adjacent nearest pixel values of the same colour when required to produce full colour information at each pixel position in the strip image and to create and store a final contiguous colour image of the portion of the specimen scanned, the final image containing full colour information at each image pixel position for each colour of the colour filter array to calculate full colour values at each image pixel position on the image strip for that colour by interpolating measured values for that colour at adjacent image pixel positions and adding the interpolated values to the image strip corresponding to that colour, and further programming the processor to assemble all of the image strips acquired to produce the final contiguous colour image.

21. A method of scanning a specimen using a scanning microscope having a light source and an optical train having at least one lens to focus light from the specimen onto a two-dimensional sensor array, the specimen being mounted on a support that is movable relative to the sensor array, the method comprising using a scanning colour filter array on the two dimensional sensor array, the sensor array having a shutter and moving the specimen and specimen support line by line relative to the sensor array during scanning and synchronizing the shutter to open, acquire a two dimensional image frame in one or more image strips of the specimen as the specimen is scanned for a plurality of lines of the sensor array, there being a plurality of image strips, each image comprising a plurality of adjacent lines of the sensor array and immediately adjacent images each shifted from one another by one line of the sensor array, the sensor array acquiring a two dimensional image each time that the shutter opens and closes, and programming a computer to receive data for the images from each of the image strips from the sensor array each time that a shutter of the sensor array opens and closes, the computer programmed to add to the data already stored, the data for newly acquired images each time that the shutter closes, thereby creating a lengthening strip image of the one or more image strips, programming the computer to access the acquired images to provide full colour information at each image pixel position and further programming the computer to assemble all of the image strips acquired to produce a final contiguous colour image, of the specimen scanned, the final image containing full colour information at each image pixel position for each colour of the colour filter array.

22. A scanning colour imaging array comprising a two dimensional sensor array, a colour filter array comprising a plurality of rows where all pixels in each row have the same colour, but the colour differs between adjacent rows, there being at least three rows of different colours, a colour sequence of the at least three rows being repeated at least once in additional rows of the scanning colour filter array by which an instrument acquires multiple images in one or more image strips for each colour of a specimen as the specimen moves line by line relative to the two dimensional sensor array, the two dimensional sensor array having a shutter synchronized to open and close with motion of the specimen relative to each line of the sensor array, the sensor array acquiring an image frame of the specimen for a plurality of lines of the sensor array, each image frame comprising a plurality of adjacent lines of the sensor array and immediately adjacent images image frames each shifted from one another by one line of the sensor array, the sensor array acquiring a two dimensional image each time that the shutter opens and closes, and a processor programmed to acquire data for the images from each of the one or more image strips from the sensor array each time that a shutter of the sensor array opens and closes, the processor programmed to add to the data already stored, the data for newly acquired images each time that the shutter closes, thereby creating a lengthening strip image of the one or more image strips, and to assemble all of the image strips to produce a final contiguous colour image, of the specimen scanned, the final image containing full colour information at each image pixel position for each colour of the colour filter array.

23. The scanning colour filter array as claimed in claim 22 wherein the at least three rows have the colours red, green and blue, with red in at least two rows, green in at least two rows and blue in at least two rows.

24. The scanning colour filter array as claimed in claim 22 wherein there is at least one additional row of a different color from the colours in the at least three rows, resulting in at least four rows of different colours, a pattern of the at least four rows being repeated at least once in additional rows of the scanning color filter array.

25. The scanning colour filter array as claimed in claim 24 wherein the colour of the at least one additional row of the at least four rows is white.

26. The scanning colour filter array as claimed in claim 24 wherein the colours of the at least four rows are red, green, blue and white.

27. The scanning colour filter array as claimed in claim 25 wherein each non-white row contains a transmission filter that matches an emission wavelength of a fluorophore.

28. The scanning colour filter array as claimed in claim 27 wherein each non-white row of the scanning colour filter array has a filter that passes only a narrow band of wavelengths near an emission peak of fluorophores.

29. The scanning colour filter array as claimed in claim 28 wherein there is a different filter in each non-white row for each of several fluorophores in the specimen.

30. The scanning colour filter array as claimed in claim 25 wherein the at least one white row passes fluorescence from the specimen and a broad band of autofluorescence.

31. The scanning microscope as claimed in claim 1 wherein the two dimensional sensor array is an sCMOS array.

32. The scanning microscope as claimed in claim 1 wherein the colour filter array is a scanning colour filter array where X is equal to at least three and N is equal to at least three and three of the colours are red, green and blue, with a pattern of the colours being repeated at least once.

* * * * *